(12) United States Patent
Howard et al.

(10) Patent No.: US 12,011,291 B2
(45) Date of Patent: *Jun. 18, 2024

(54) NON-INVASIVE WEARABLE BIOMECHANICAL AND PHYSIOLOGY MONITOR FOR INJURY PREVENTION AND REHABILITATION

(71) Applicant: GEORGE MASON RESEARCH FOUNDATION, INC., Fairfax, VA (US)

(72) Inventors: Marissa A. Howard, Richmond, VA (US); Lance A. Liotta, Bethesda, MD (US); Rachel Naidich, Fairfax, VA (US); Matthew Luu Trang, Nokesville, VA (US); Ish Sethi, Chantilly, VA (US); Rebecca Woodhouse, Oakton, VA (US); Kshamata Neupane, Haymarket, VA (US)

(73) Assignee: GEORGE MASON RESEARCH FOUNDATION, INC., Fairfax, VA (US)

( * ) Notice: Subject to any disclaimer, the term of this patent is extended or adjusted under 35 U.S.C. 154(b) by 12 days.

This patent is subject to a terminal disclaimer.

(21) Appl. No.: 17/651,661

(22) Filed: Feb. 18, 2022

(65) Prior Publication Data
US 2022/0167918 A1  Jun. 2, 2022

Related U.S. Application Data

(63) Continuation of application No. 16/169,295, filed on Oct. 24, 2018, now Pat. No. 11,284,838.
(Continued)

(51) Int. Cl.
*A61B 5/00* (2006.01)
*A61B 5/01* (2006.01)
*A61B 5/11* (2006.01)

(52) U.S. Cl.
CPC ......... *A61B 5/6828* (2013.01); *A61B 5/0024* (2013.01); *A61B 5/0053* (2013.01);
(Continued)

(58) Field of Classification Search
CPC ......... A61B 5/01; A61B 5/015; A61B 5/1072; A61B 5/4528; A61B 5/4585;
(Continued)

(56) References Cited

U.S. PATENT DOCUMENTS 6,002,965 A  12/1999  Katz et al.
6,360,615 B1   3/2002  Smela
(Continued)

FOREIGN PATENT DOCUMENTS

WO  2014209916 A1  12/2014
WO  2016058053 A1   4/2016

OTHER PUBLICATIONS

Medvecky, et al. "Surgical approaches to the posteromedial and posterolateral aspects of the knee." JAAOS—Journal of the American Academy of Orthopaedic Surgeons 13.2: 121-128. (Year: 2005).*

*Primary Examiner* — David J. McCrosky
(74) *Attorney, Agent, or Firm* — WC&F IP

(57) ABSTRACT

A wearable device measures, tracks, and monitors a wearer's physical physiological conditions during a rehabilitation period. Metrics such as temperature, patellar shifting, limb circumference, and acceleration may be collected. Changes in monitored conditions may be assessed for detecting medical abnormalities which require specialized attention, including for example embolisms or infections. A networked communication system and various user interfaces may be used for medical support personnel and patients alike to stay updated with the patient's rehabilitation progress and to make adjustments in a patient's individual rehabilitation program.

18 Claims, 19 Drawing Sheets

Related U.S. Application Data

(60) Provisional application No. 62/576,361, filed on Oct. 24, 2017.

(52) U.S. Cl.
CPC ............ *A61B 5/015* (2013.01); *A61B 5/1107* (2013.01); *A61B 5/1126* (2013.01); *A61B 5/4528* (2013.01); *A61B 5/4585* (2013.01); *A61B 5/4848* (2013.01); *A61B 5/6824* (2013.01); *A61B 5/6829* (2013.01); *A61B 5/7275* (2013.01); *A61B 5/746* (2013.01); *A61B 5/0048* (2013.01); *A61B 5/1114* (2013.01); *A61B 5/112* (2013.01); *A61B 5/4519* (2013.01); *A61B 5/7465* (2013.01); *A61B 2503/08* (2013.01); *A61B 2503/10* (2013.01); *A61B 2505/09* (2013.01); *A61B 2562/0219* (2013.01); *A61B 2562/0247* (2013.01); *A61B 2562/0261* (2013.01); *A61B 2562/0271* (2013.01); *A61H 2230/08* (2013.01); *A61H 2230/50* (2013.01)

(58) Field of Classification Search
CPC ... A61B 5/4824; A61B 5/4833; A61B 5/6828; A61B 5/0053
See application file for complete search history.

(56) References Cited

U.S. PATENT DOCUMENTS

| | | | |
|---|---|---|---|
| 9,314,159 B2 | 4/2016 | Lyon et al. | |
| 11,284,838 B2 * | 3/2022 | Howard | A61B 5/6828 |
| 2007/0273504 A1 | 11/2007 | Tran | |
| 2008/0161731 A1 | 7/2008 | Woods et al. | |
| 2009/0281412 A1 | 11/2009 | Boyden et al. | |
| 2012/0184878 A1 | 7/2012 | Najafi et al. | |
| 2012/0203078 A1 | 8/2012 | Sze et al. | |
| 2014/0109304 A1 | 4/2014 | Kwan et al. | |
| 2015/0088043 A1 | 3/2015 | Goldfield | |
| 2015/0328032 A1 | 11/2015 | Walker et al. | |
| 2016/0242646 A1 | 8/2016 | Obma | |
| 2017/0042467 A1 | 2/2017 | Herr et al. | |
| 2017/0367644 A1 * | 12/2017 | Sharman | A61B 5/1121 |

* cited by examiner

Algorithm Flow chart of Data collection, user interface Integration and early warning notification system:

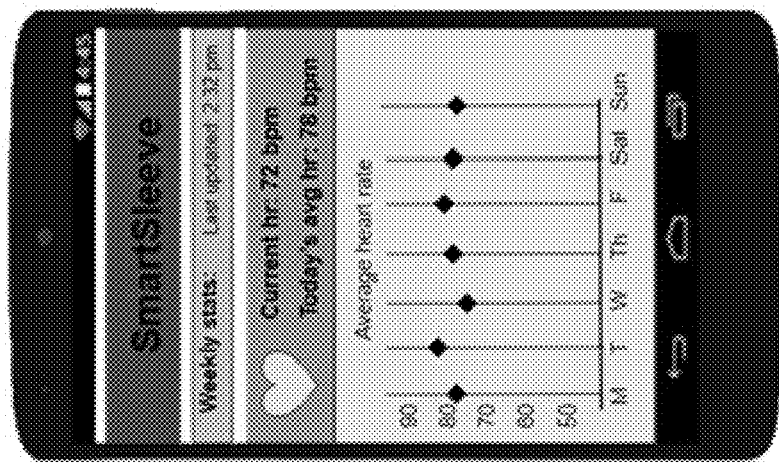
Figure 9C Weekly Summary
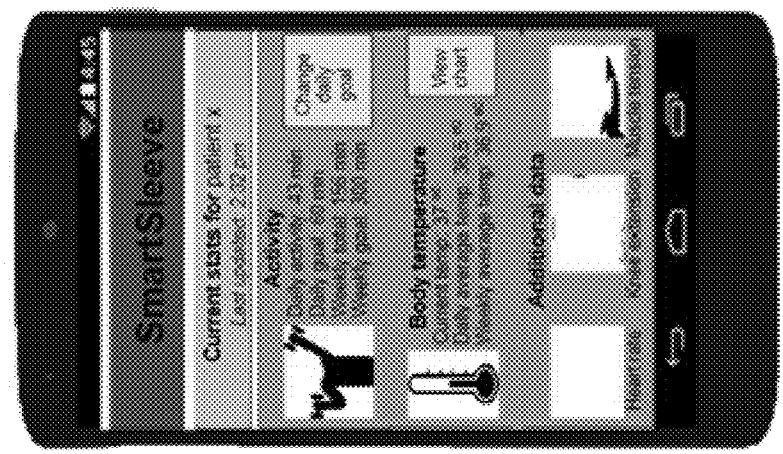
Figure 9B Physician UI
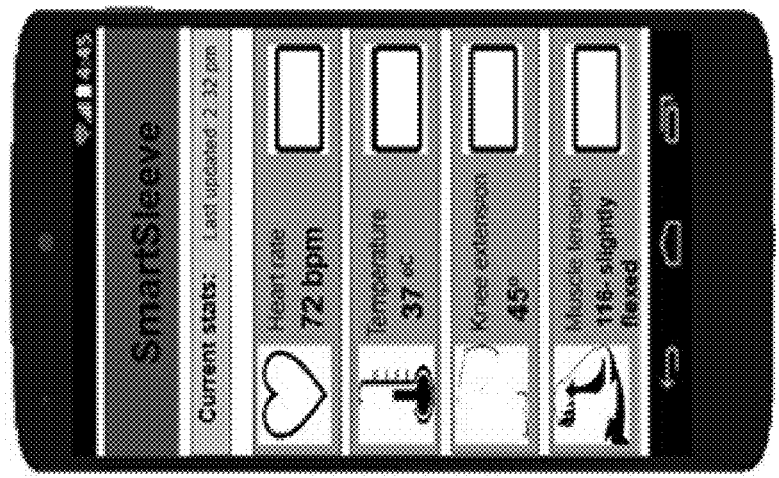
Figure 9A Patient UI

NON-INVASIVE WEARABLE BIOMECHANICAL AND PHYSIOLOGY MONITOR FOR INJURY PREVENTION AND REHABILITATION

CROSS-REFERENCE TO RELATED APPLICATIONS

This application is a continuation of U.S. patent application Ser. No. 16/169,295, filed Oct. 24, 2018. This application claims the benefit of U.S. provisional patent application No. 62/576,361, filed Oct. 24, 2017, the complete contents of which are herein incorporated by reference.

STATEMENT REGARDING FEDERALLY SPONSORED RESEARCH OR DEVELOPMENT

This invention was made with government support under grant number AR068436 awarded by the National Institutes of Health. The government has certain rights in the invention.

FIELD OF THE INVENTION

The invention generally relates to wearable technology usable to measure and monitor physiological and activity information about a user for applications such as post-injury or post-operative rehabilitation.

BACKGROUND

When surgical procedures are necessary to treat problems with the musculoskeletal system (e.g. ligament tears), a high percentage of patients do not have an optimal outcome. Instead they are functionally impaired by poor joint mobility and limited range of motion. For civilian or military personnel this causes a delay in a return to active duty and reduced duty performance. Such poor outcomes are often caused by failure to detect and treat injury complications, and by poor compliance during rehabilitation and post injury follow-up. Many complications can arise during rehabilitation such as but not limited to swelling, blood clots, and infection.

When active duty service members suffer a knee injury such as meniscal tears, ACL, PCL, MCL, LCL repairs, or patellar dislocations, the estimated time to return to full active duty following rehabilitation ranges from 9 to 24 weeks. Moreover, due to shortages of physical therapists or rehabilitation specialists in the military, those with the most severe knee injuries are preferentially treated. Therefore, soldiers with minor knee injuries are more likely to undergo an imperfect rehabilitation plan.

The physical demands and collision forces experienced by active duty military personnel in training and operational environments generates an increased risk of knee injuries. Currently, the incidence and prevalence of knee injuries in training and service are unnecessarily high, thus impairing readiness and increasing the rate of removal from active duty.

Joint replacement surgeries are expected to rise ten times their current rate. By 2030, it is estimated that 11 million individuals will require a joint replacement surgery. Current post-operative rehabilitation methods provide short intervals of guided care, after which the patient is expected to perform self-care exercises in order to heal. Current rehabilitation devices focus on enhancing support via immobilization or compression.

Even though patients are instructed to start physical therapy the day after their surgery, or following an injury, a physical therapist can only spend time with the patient for a limited number of hours per week. Low patient compliance to perform at-home rehabilitation exercises, as prescribed, has been a major hurdle facing orthopedic surgeons and physical therapists. A patient's unwillingness to perform prescribed exercises or, for Active Duty personnel, a desire to push too hard too fast increases the likelihood of risk of re-injury, muscle atrophy, joint stiffening, and life-threatening complications. Additionally, inadequate rehabilitation is shown to lead to increased risk of osteoarthritis (OA) development and reduced final range of motion (ROM) of the joint. Potentially fatal complications can arise in the off-time when the patient is not being seen by a treating physician or rehabilitation specialist. All of these issues are contributing factors to extended delay prior to return to the workforce for Active Duty personnel and Veterans after knee injury/surgery.

Current rehabilitative tools for surgeries such as total knee replacement are rigid braces which provide no diagnostic information and often force the patient to "compensate" to accommodate the constraints of the brace. Alternative rehab assistive devices are needed for improving the quality of rehab care and shortening the time for full rehabilitation of personnel with acute knee injuries, including strains, sprains, dislocations, and ligament tears, as well as for treating many other musculoskeletal injuries.

SUMMARY

An objective of some embodiments is to provide end users with a device or system of sensors and software that can collect meaningful physiological measurements for rehabilitative purposes.

Another objective of some embodiments is to reduce rehabilitation time and improve long term rehabilitation goals. These goals may be achieved with humans and with various other animals (e.g., horses, pigs, cows, cattle, dogs, cats, other ranch animals, other domestic animals, wild animals, etc.).

Another objective of some embodiments is to provide an alert system for users by which users are alerted to a risk or presence of a medical condition requiring attention, such as but not limited to an infection, embolism, and effusion, based on monitoring of a part of the body (e.g., a joint) during a rehabilitation or recovery period, for example.

Another objective is to monitor and instruct adjustment of wearable position with respect to a patient's patella and/or to monitor and detect patellar deviations. Some embodiments comprise one or more pressure sensors configured to detect pressure indicating the location, movement, and circumference of a patient's patella.

According to an aspect of the invention, some embodiments comprise a wearable device (i.e., "wearable") configured to monitor patient parameters such as but not limited to knee movement, heart rate, temperature, and muscle flexing. The device may be configured to perform or assist in performing a noninvasive method of monitoring joint rehabilitation by utilizing unique sensors and a learning algorithm.

Some exemplary embodiments may include one or more of (e.g., all of) the following sensors to monitor a patient: stretch sensors, accelerometer, gyroscope, temperature, and heart rate monitor. All of these sensors can provide information regarding patient movement, swelling, heart rate, infection, and force applied with each step.

According to another aspect, some embodiments provide the patient and/or doctor feedback on the patient's vitals and movements in order to prevent deep vein thrombosis (DVT) or infection and/or to ensure that the patient follows the recommended therapeutic exercises. In addition, embodiments may provide custom feedback for the patient to instruct him or her on exercises and knee usage. In some embodiments, a healthcare provider (e.g., doctor, physical therapist, surgeon, nurse, etc.) may aid the patient with device calibration after surgery (e.g., a total knee replacement (TKR)). An exemplary electronic application in communication with the wearable worn by the patient may provide the doctor with early warning notifications regarding potential complications as well as to provide recurring reports (e.g., daily, weekly, monthly, etc.) to track the patient's ability to achieve exercise goals set by or with the input of the healthcare provider.

According to an aspect of some embodiments, a patient joint monitoring system is provided which can detect swelling, infection, and/or blood clots. The system may track body movements to ensure proper joint use. The system may include additional sensors such as ultrasound or infrared to detect DVT.

Some embodiments may comprise non-invasive wearable devices which provide real-time physiological and clinical measurements with wireless embedded sensing technology with advantages of improving operational readiness and soldier deployability, or improving civilian rehabilitation following injury or surgery measurable in: a) reduced duration of rehabilitation and rapid return to duty or employment, b) absence or substantial reduction in the incidence of impaired physiologic function, and c) reduction in the risk of unattended medical complications occurring during rehabilitation regimens and outside clinic visit time. Rehabilitation goals may include but are not limited to full range of motion, lack of pain, strength and stability substantially equivalent to pre injury state of the joint.

Some embodiments involve non-invasively and wirelessly measuring and monitoring a set of physiologic and health parameters associated with both joint function and joint health, while continually learning and updating the system to the individual.

Exemplary systems will improve patient outcome in terms of joint mobility and range of motion while reducing recovery time following a knee injury or knee surgery.

A wearable's microelectronics may include sensors, data storage, battery, and wireless communication antennas (e.g., WiFi and/or Bluetooth).

An exemplary device is configured to communicate in real-time with the patient and rehabilitation specialist. A custom mobile app for Android and iOS operating systems graphically displays the parameters requested by their rehab specialist.

Exemplary embodiments may provide simultaneous measuring and tracking, monitoring of joint heath, and learning of a patient's individual knee kinematics. Information may be transmitted in real-time, wirelessly, and longitudinally, to the treating physician and to the phone application of the patient, and displayed in a graphic format that is easy to understand by the patient and medical personnel.

Some devices may include a patella position tracking element. In addition to the superior and inferior motion of the patella, the patella also tracks lateral-medial during tibiofemoral extension to flexion. The type of measurements for the patella proposed for the wearable device, in all four directions, is an innovative approach to identify situations in which excessive medial or lateral motion occurs during flexion, since the patella remains relatively centered on the trochlea in normal or athletic use.

An exemplary method for a knee wearable may comprise securing a flexible wrap to a patient, the flexible wrap comprising a plurality of pressure sensors; positioning the flexible wrap such that at least one respective pressure sensor is arranged at each of a superior, inferior, lateral, and medial position relative a patella of the patient; determining a position of the wearable with respect to the patient's knee by monitoring outputs of the pressure sensors; and alerting the patient to adjust a position of the flexible wrap based on the determined position. The method may further comprise monitoring patellar deviations with the pressure sensors.

Exemplary wearables may be customized in shape, fit, size, etc. for different joints or parts of the body including but not limited to shoulder, ankle, hip, wrist, elbow, neck/spin (cervical).

Exemplary wearables may configured for use with humans, equine (e.g. race and working horses), and other species (e.g., canine, feline, etc.).

BRIEF DESCRIPTION OF THE DRAWINGS

FIGS. 9A to 9C are example interfaces.

DETAILED DESCRIPTION

Referring now the drawings, the drawings depict and characterize exemplary medical apparatus and related methods of operation and use. At least in some embodiments, the medical apparatus may be characterized as a wearable, which implies the device is configured to be worn by a subject (e.g., a patient) and has electronics such as certain biosensors (sensors capable of measuring certain signals relating to physiology, for example). Some of the embodiments are especially configured to be worn on or about a joint. For illustrative purposes, some of the drawings focus on a sleeve configuration wearable on or about the knee joint.

Figure 1A:
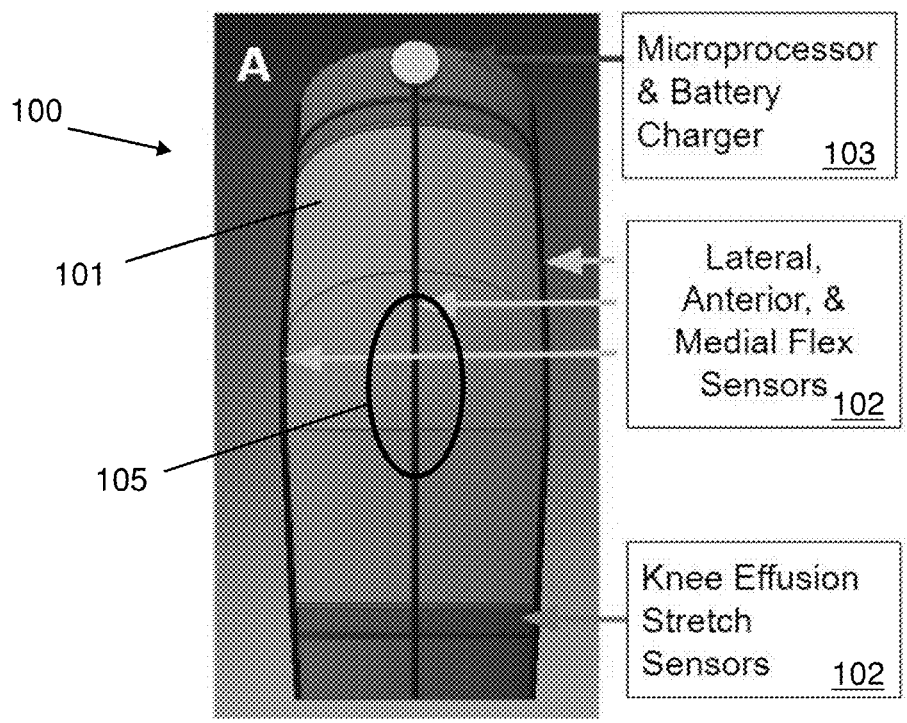
FIGS. 1A and 1B are an exemplary wearable.

FIG. 1A depicts a wearable 100, in particular a wearable configured as a sleeve sized to fit over a human leg and grip the leg using elastic compression. The wearable 100 may be a joint rehabilitation soft flexible wrap or sock knee legging, for example. The term wrap includes sleeves, socks, and like terms. These terms may sometimes be used interchangeably. These terms may be used to refer to a device which is configured to fit over a joint. The wearable 100 may be characterized as a portable joint monitoring system configured for prolonged use, e.g., use during which an end user may conduct everyday tasks away from home or the office of a clinician or therapist. While the wearable 100 is especially well suited for knee rehabilitation, variations of the invention may be configured for other joints (e.g., elbow, wrist, ankle, hips, shoulder, etc.) without deviating from what is disclosed herein. Embodiments may be configured for different sized patients (e.g., smaller sizes for children and larger sizes for adults) and different categories of patient (e.g., human, equine, dog, etc.).

The wearable 100 may be configured to non-invasively measure and/or monitor a number of different attributes a patient, including but not limited to patient movements and joint health. To make measurements and perform monitoring the wearable 100 may comprise a plurality of sensors 102, a processor 103 with decision making logic for processing and extracting useful information from the sensor data, and output mechanisms for instructing, alerting, or otherwise communicating with a user (e.g., the end user or a medical practitioner). An exemplary wearable 100 may provide or assist in providing a doctor-patient joint monitoring system to not only promote joint improvement, but also provide alerts to potential serious (e.g., potentially fatal) common complications such as venous thrombosis and post-surgical infection and swelling. Alerts and alarms may be individualized.

The wearable 100 comprises a textile material 101. The textile material 101 may be elastic to affix the wearable to a patient in a state of use. A wearable 100 may however have additional or alternative affixing features such as hook-and-loop fasteners (e.g., Velcro®) which offer flexible and adjustable sizing. The textile material 101 may be a medically approved biomaterial and may be waterproof. For patient comfort and improved patient compliance, the textile material 101 may be configured to minimize or eliminate discomfort sometimes associated with form-fitting wearables. For example the textile material 101 may be relatively soft. The textile material 101 may consist of or comprise an antibacterial mesh that provides breathability and minimizes a risk of infections.

The wearable 100 may be water resistant or waterproof. Since it may be worn for extended durations of time (e.g., at least an hour, at least a day, at least a week), exposure to moisture from the environment or simply from user sweat is expected. Sensors may be encapsulated, e.g. silicone encapsulated.

An exemplary wearable 100 comprises one or more of (in some cases all of) the following sensors 102: accelerometer(s), gyroscope(s), heart rate monitor(s), inertial measurements unit(s), stretch/flex sensor(s), pressure sensor(s), and temperature sensor(s). Some individual sensors may perform more than one of the aforementioned functionalities. Groups of sensors may be configured together as one or more sensor arrays.

Sensors of the wearable 100 may be permanently incorporated with the textile 101, removably attachable with the textile 101, or some combination thereof. Whether integrated or embedded or removable, most and preferably all of the sensors are sized and arranged to permit the user to conduct their ordinary daily movements and on the go activities unencumbered (e.g., walk, exercise, drive, run, etc.).

Data from the sensors is processed and interpreted to determine one or more of: joint kinematics, biomechanical forces, patient movement, effusion (swelling), heart rate, infection, thromboembolism, misalignment, impact, loading forces (e.g., step impact), biomechanical acceleration forces (level of acceleration of a joint), range/direction/frequency of motion, temperature differentials, muscle activity, joint deviations (e.g., patellar deviations)

Data may be collected by one or more of the sensors continuously, periodically, at regular or irregular interval, intermittently, or cyclically. In any case, longitudinal data is advantageous when the wearable 100 is used for long term treatments or rehabilitation goals. Collected data may be physiological, biomechanical, or some combination of these. Data may be collected, processed, and output in substantially real time.

Following are a few example sensors, measurements, and assessment that may be made with a wearable 100. Knee kinematics and biomechanical measurements may be assessed using elastomeric resistive stretch sensors and/or flex sensors measuring ROM (degree of flexion/extension), joint angles, planes of motion (sagittal, frontal), step width, length, frequency, and gait speed may be used to evaluate gait assessment. Knee effusion (symmetric and asymmetric) may be assessed using circumferential elastomeric resistive stretch sensors measuring degree of surrounding joint tissue effusion may be used to assess phantom model with adjustable degrees of effusion. Temperature inhomogeneities may be assessed using an array of NTC thermistors measuring positional temperature differentials and rate of temperature changes in relation to a ground state temperature surrounding the patella. Patellar contours may be assessed using force/pressure sensors measuring patellar deviations and proper alignment of device. Inertial motion may be assessed using a 9 DOF IMU measuring ROM, step angle/plane, step time, traversed distance/terrain.

Figure 1B:
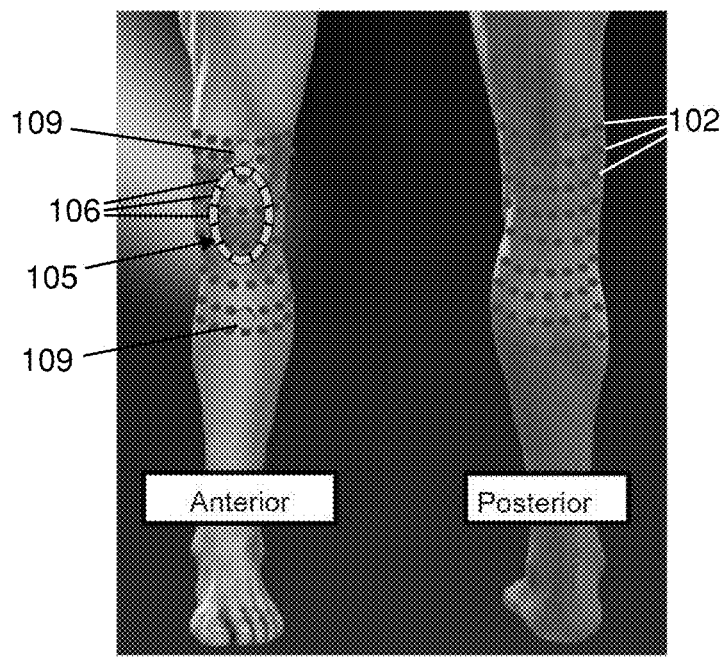

FIG. 1B shows the sleeve 100 while worn by a human about the knee. The textile material 101 is not shown to permit clear depiction of sensor arrangement. A number of thermistors (and/or other types of temperature sensors) (circles 107 in FIG. 1B) are positioned in an array about the sleeve 100 and, correspondingly, the patient's knee. The thermistor array wraps circumferentially about the joint and span surface area (of the sleeve 100 and of the patient) of the joint itself as well as to all sides of the joint (anterior, posterior, lateral, medial, proximal, distal). The collective temperature readings from the thermistors may be used by the controller to produce a thermal heat map. The temperature measurements are interpolated and converted to the heat map. The heat map may itself be an output. The heat map may also be further processed to identify a presence or lack of an internal condition of the patient. For example, the heat map may be processed to identify an anomaly such as an infection or thrombosis.

Temperature measurement profiles such as thermal maps from the surface of the knee and surrounding regions of the leg may be used to assess physiologic temperature differences caused by anatomical structures, muscle blood flow, vascular structures and tissue frictional heating.

For knee applications, the sleeve 100 may include a pressure sensitive patellar position monitor or, more generally, a patella sensor 105, sometimes referred to herein as a "patellar donut" as shorthand (though it needn't necessarily be "donut" shaped in all embodiments).

Figure 2A:
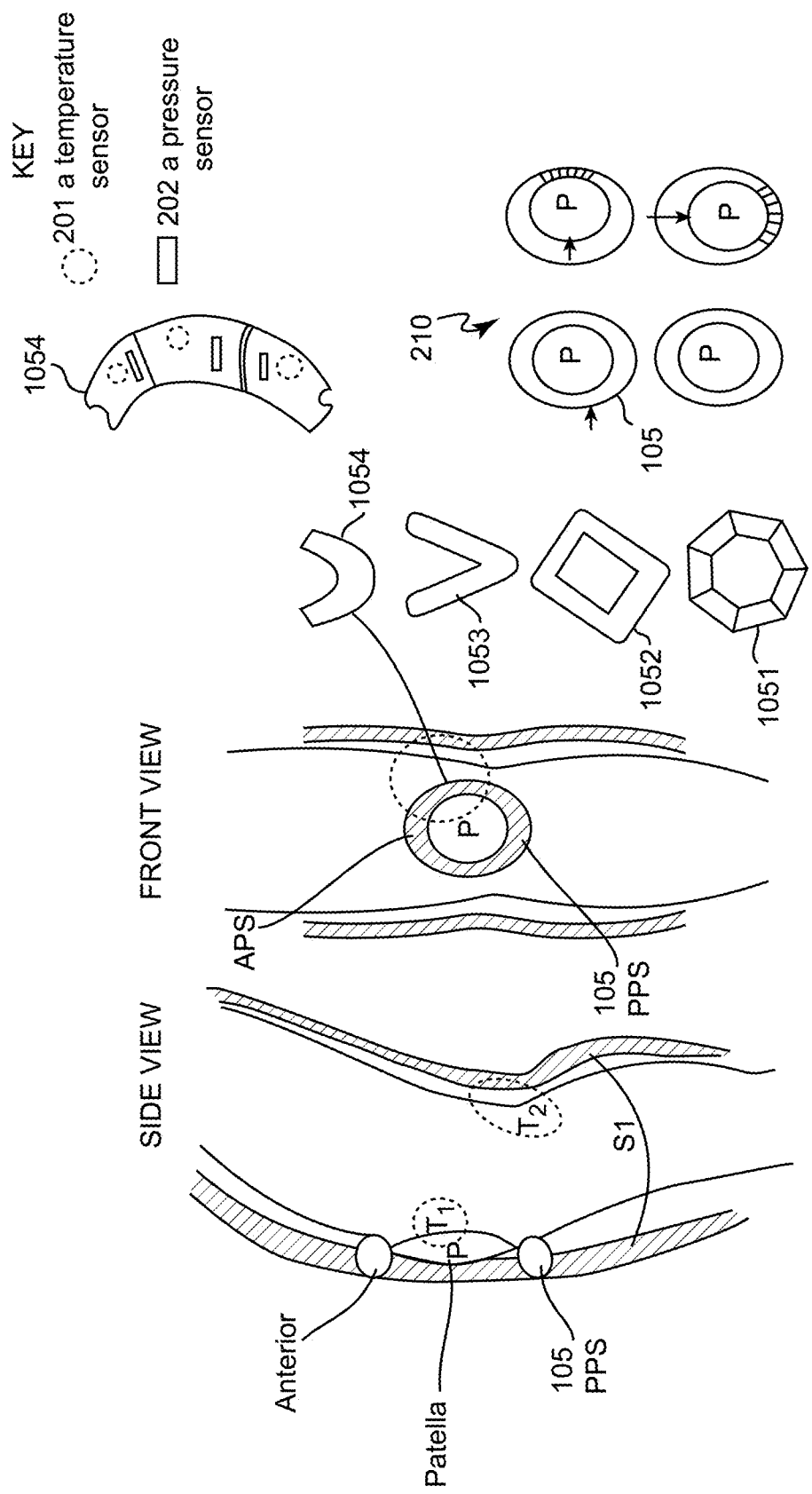
FIGS. 2A and 2B are examples of exemplary patella sensors.

FIGS. 3A and 3B show aspects of a patella sensor 105 arranged on a subject's leg (which includes a knee with a patella P). The patella sensor 105 comprises one or more pressure sensors 202 and temperature sensors 201 configured to detect pressure and temperature, respectively, about the circumference of the patient's patella (generally at a plurality of localities, including at least positions superior, inferior, lateral, and medial to the subject's patella). Additional sensors at additional locations may also be included. For example, some embodiments include a second temperature sensor at a backside of the knee for measuring a temperature T2 which may be compared with one or more temperatures T1 sensed at the circumference of the patella P. Generally, a patella sensor 105 may include sensing elements for one or more (e.g., all) of temperature, pressure, dielectric constant, impedance, and deformation. FIG. 2A includes four non-limiting alternatives for configurations of patella sensors 105, labeled respective as patella sensors 1051, 1052, 1053, and 1054. As illustrated, a patella sensor 105 may be donut shaped, circular, enclosed, open, pyramidal, diamond shaped, V shaped, U shaped, or some other configuration. A patella sensor 105 may be used together with, for example, one or more circumferential stretch sensors S1. Subdiagram 210 shows how a change in the relative alignment/positions of the patella P and patella sensor 105 is sensed by one or sensing elements (e.g., pressure sensors 202), indicated in 210 by shading within sensor 105. The sensed change in alignment can trigger an alert or instruction that adjustment of the sleeve 100 is required.

Figure 2B:
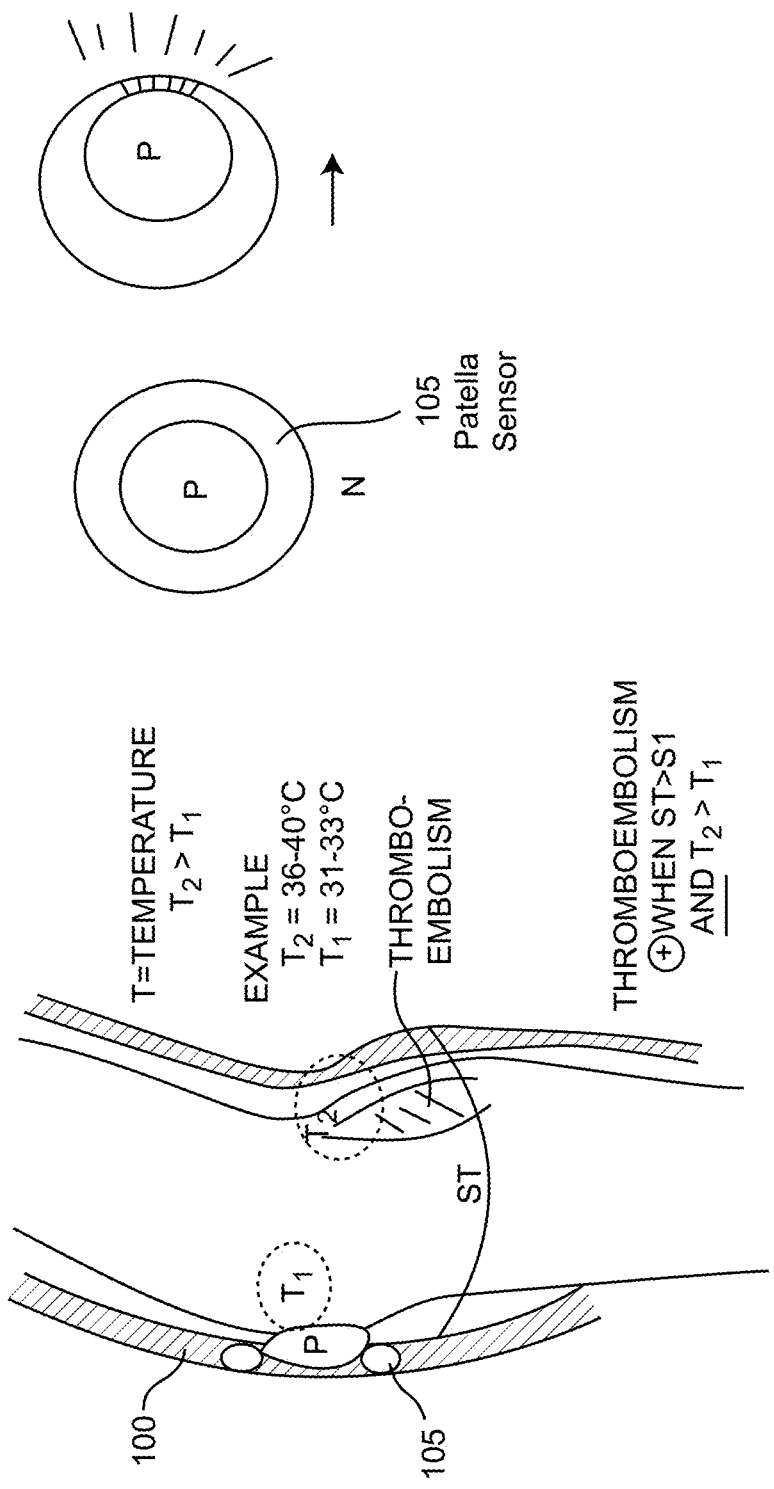

The left side of FIG. 2B is illustrative for an exemplary method for diagnosing embolism or infection in a subject's leg. Such a method may comprise placing a wrap/sleeve 100 about a knee of a subject, the wrap comprising a plurality of first sensors positionable to sense temperatures T1 about a circumference of a patella P of the knee and at least one second sensor positionable to sense temperature T2 at a back of the knee; comparing temperatures from the first and second temperature sensors; and identifying a presence of embolism or infection in the subject's leg based on the comparison.

The right side of FIG. 2B is illustrative for an exemplary method for positioning a wearable sensing device on a subject's leg. Such a method may comprise placing a wrap/sleeve 100 with a patella sensor 105 about a knee of a subject, the wrap comprising a plurality of sensors for measuring one or more physical or physiological parameters; urging alignment of a depression in the wrap with a patella of the knee, at least some of the plurality of sensors being arranged about a circumference of the depression; and monitoring or confirming an alignment of the patella with the depression based on one or more of (i) changes in an output of at least one of the circumferential sensors and (ii) differences among outputs of two or more of the circumferential sensors.

In use the patellar sensor 105 is configured to guide or contribute to guidance of a user aligning the device in the correct individualized orientation. The patellar force sensor is also used during the device operation to detect abnormal or pathologic deviations of the patellar position or orientation that may reflect injury or abnormal directions of patellar forces during rehabilitation. In some exemplary embodiments, the patellar donut is a deformable circumferential pillow or cushion molded to an individual's patella to conform or surround the patella to measure patellar physical deviations in all planes of motion with embedded sensors. The patellar donut 105 provides the sleeve 100 with measurements of patellar deviations. In an exemplary configuration, circumferential elastomer conductive resistive stretch sensors are positioned superior and inferior to the patella to detect variations of joint effusion. Additionally, the stretch sensors may be combined with (silicon encapsulated) flex sensors positioned medially, laterally, and anteriorly to measure ROM and planar motions. In some embodiments the patellar donut is divided radially into series of chambers 106 filled with conductive fluid or gel (FIG. 1B shows a patellar donut 105 having 12 chambers 106; other embodiments may have fewer than 12 or greater than 12, e.g., 4, 6, 8, 10, 16, or 32 chambers). Relative differences in the resistance/impedance levels within each chamber reflects the conformation of the patellar sensor for calibration. Exemplary applications and uses for a patella sensor 105 are described below in Example 3.

Temperature wrap-around knee thermal mapping by a wearable device and patella displacement force mapping by the wearable device together permit physiologic monitoring of joint tissues and, with respect to the knee, patellar dynamics and patellofemoral pain. An important measurement set is the relative differences in temperature over the surface of the joint matched with stretch and force sensors corresponding to the temperature reading locations. By pairing these measurements a pathologic swelling may be detected by sensing an increased temperature associated with increase stretch over the underlying swollen region.

The sensors of the wearable 100 may include one or more inertial measurement units (IMUs). An IMU may be, for example, a 9 degree of freedom (DOF) IMU. The IMU may be configured to detect forces and motion in various planes. FIG. 1B depicts two exemplary positions for two respective IMUs 109. One IMU is proximal to the joint, and another IMU is distal to the joint. IMUs are particularly well suited for detection of gait abnormalities.

Power for a wearable 100 may be provided by, for example, a power supply such as a lithium ion gel battery. Sensors may be low power (e.g., low voltage) to permit extended use between battery charges. Power supplies, e.g., batteries may be interchangeable, or an integrated power supply may be used which is recharged by wire or wirelessly (e.g., by inductive charging).

The wearable 100 may include one or more embedded or removable storage devices (e.g., solid state memory). The storage devices may be volatile and/or non-volatile. The storage may comprise executable instructions which, when executed by the controller, cause it perform functionalities described herein, among other possible functions. For example a controller executing stored instructions may provide processing and determinations based on data being collected from the sensors in real time. The controller, executing stored instructions, may for example detect localized elevations in body temperature by monitoring the temperatures sensed by the temperature sensors at the at least two different positions on the wrap, detect swelling by monitoring the strain sensed by the at least one stretch sensor, identify a risk of thrombosis or infection when one or more of localized elevation in body temperature and swelling are detected, and/or provide an alert to one or more of the patient and a heath care professional of the identified risk.

Figure 3:
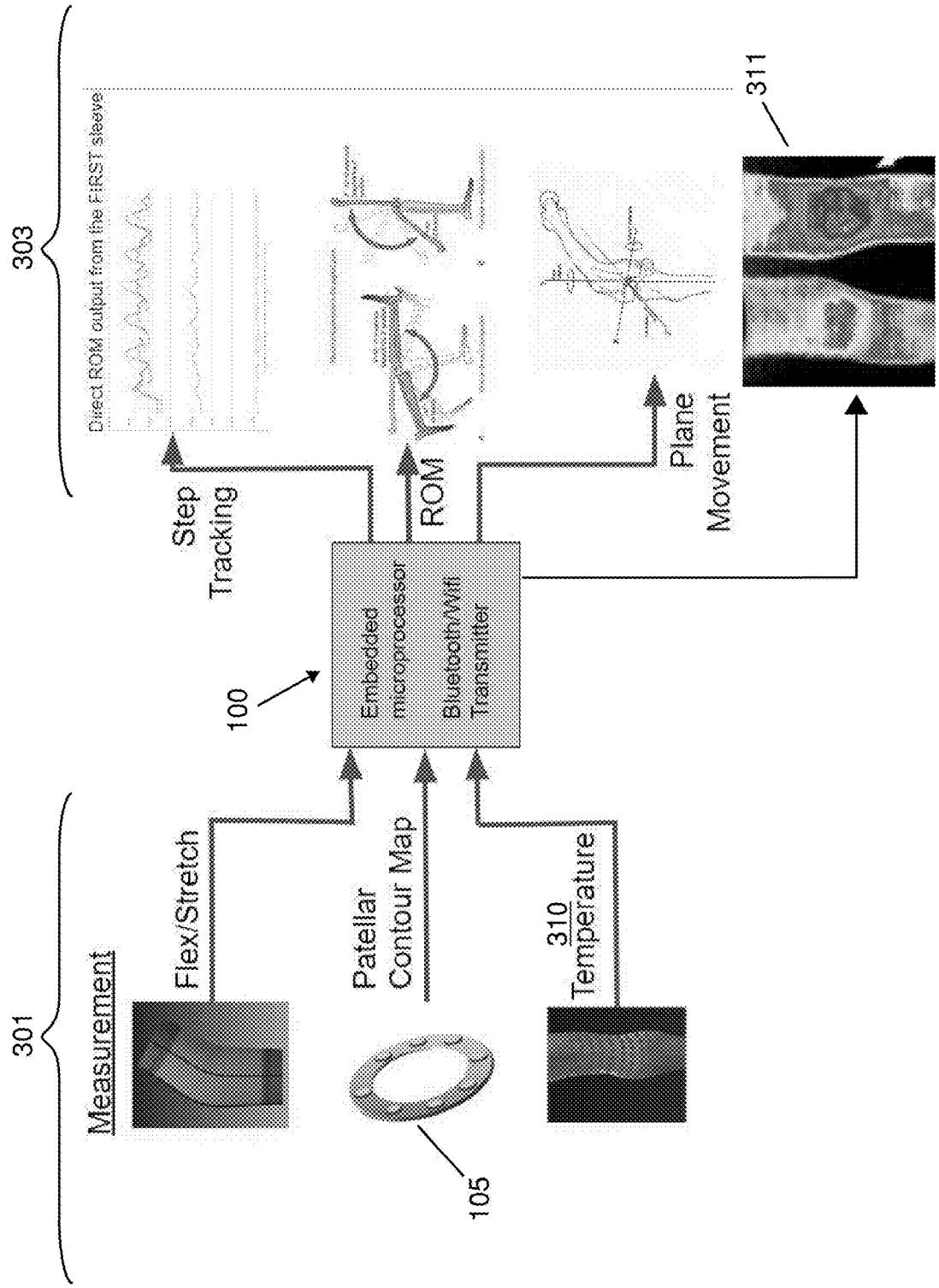
FIG. 3 illustrates information flow and production from data collection to analysis to output of joint information for users.

FIG. 3 illustrates information flow and production from data collection 301, to analysis, to output of joint information for users 303. While original data points (e.g., temperature readings 310 from individual thermistors) may be provided to users, the processed information (e.g., heat map 311) derived from the original measurements may often be of greater value and is advantageous as an element of final output to users.

The wearable 100 may comprise an "onboard" computer or controller, e.g., a processor or microprocessor and supporting circuitry like data storage devices and a power supply e.g., battery. The controller may be, for example, a CPU or microprocessor (a fully operational integrated computer chip). The controller may be located in a superior region of the device. The controller may be fully programmable and encrypted to allow for modifications or personalization of rehabilitation exercises for the user and physician.

Figure 4A:
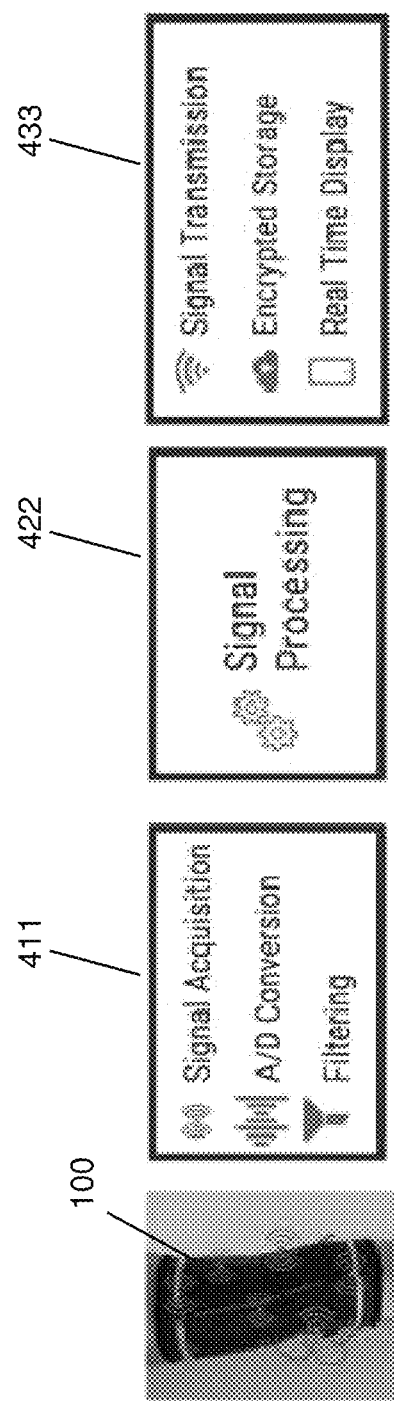
FIG. 4A is a block diagram generally illustrating data collection, signal processing, and transmission.

FIG. 4A is a block diagram generally illustrating data collection 411, signal processing 422, and transmission 433. Data collection 411 may be mainly or entirely "on device" that is to say performed by sensors attached or integrated with the wearable 100. Signal processing 422, on the other hand, may be performed on device, off device, or some combination thereof. For example, processor(s) and storage may be part of the wearable 100 and perform signal processing 422. Alternatively or in addition, one or more processors and storage media may be off device (e.g., in a user's mobile device like a smartphone, in a cloud based server, etc.) and perform some or all of signal processing 422. In these cases the signal processing 422 and its supporting structures are remote from and not on the wearable 100. In short, a wearable 100 may collect physiological and medical data and in real time transmit that data in unprocessed or processed form to remote devices via radio telemetry or direct download onto a protected server, for example.

In some embodiments the wearable 100 has wireless capabilities, e.g., antenna and supporting circuitry for transmitting data collected and/or determined by the wearable 100 wirelessly. Suitable wireless standards and technology are known and may be employed, including but not limited to WiFi and Bluetooth.

Secure network technology may be used for longitudinal remote monitoring and wireless transmission of data between, for example, an attending physician and the patient. Patient data, raw or processed, may be stored in one or more of the wearable 100, end user devices (like a patient's smartphone or computer), local servers, remote servers, cloud servers, or some combination thereof. Data may be stored for a fixed amount of time, e.g., one month, and then automatically removed. This can be particularly advantageous for storage on a wearable 100 where storage space comes at a premium to ensure the size, weight, power consumption, and cost are minimized. Stored data may of course be encrypted for patient privacy concerns.

While physical and physiological data may be transmitted to medical support personnel like doctors and therapists, these entities may transmit data back to the end user. For example, rehab program and exercise regiments may be updated over the course of a patient using a wearable 100. Real time data may be compared with historic data to track progress over time and update medical care over time. In short the networked communication system may be used for individualized care without a patient making physical trips to a doctor or therapist's office for periodic sessions.

Figure 4B:
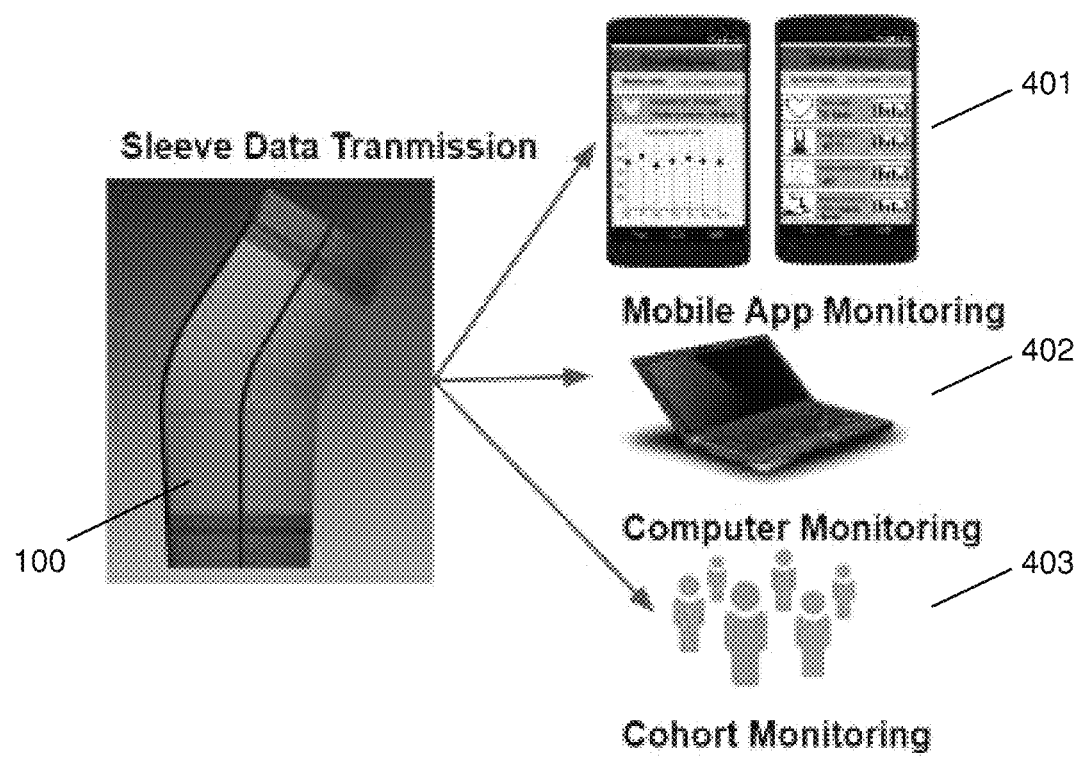
FIG. 4B is a diagram illustrating the supply of information to a variety of different users, including the wearer of the wearable via a mobile app or computer as well as including a medical cohort.

FIG. 4B is a diagram illustrating the supply of information to a variety of different users, including the wearer of the wearable 100 via a mobile app 401 or computer 402 as well as including a medical cohort 403. "Users" may include subjects that actually wear a wearable 100, caretakers, medical practitioners (e.g., doctors, nurses, technicians), therapists (e.g., physical therapists), and others.

Data and other outputs of a wearable 100 may be supplied to one or more users using any of a variety of interfaces. Generally it is advantageous that interfaces be presented in friendly and easy to understand configurations. Devices suited for user interface are man, including but not limited to smartphones, tablets, display, projectors, general purpose computers, special purpose computers, and other wearables (e.g., a smartwatch). A wearable 100 may itself have a user interface attached or imbedded therewith but needn't in all cases. Given the prevalence of smartphones, a wireless communication link between a wearable 100 and smartphone may be used which allows the wearable 100 influence or control over a user interface displayed our otherwise output on the smartphone.

User interface output may come from sources other than the wearable 100. For example, specialists such as doctors or rehabilitation specialists may send information over a network to an end user interface, e.g., an interface of the person wearing a wearable 100. For example exercise routines may be provided for an end user to perform while wearing the wearable 100. Data may be collected during the exercise which is then transmitted back to the specialist for interpretation or monitoring.

Figure 5:
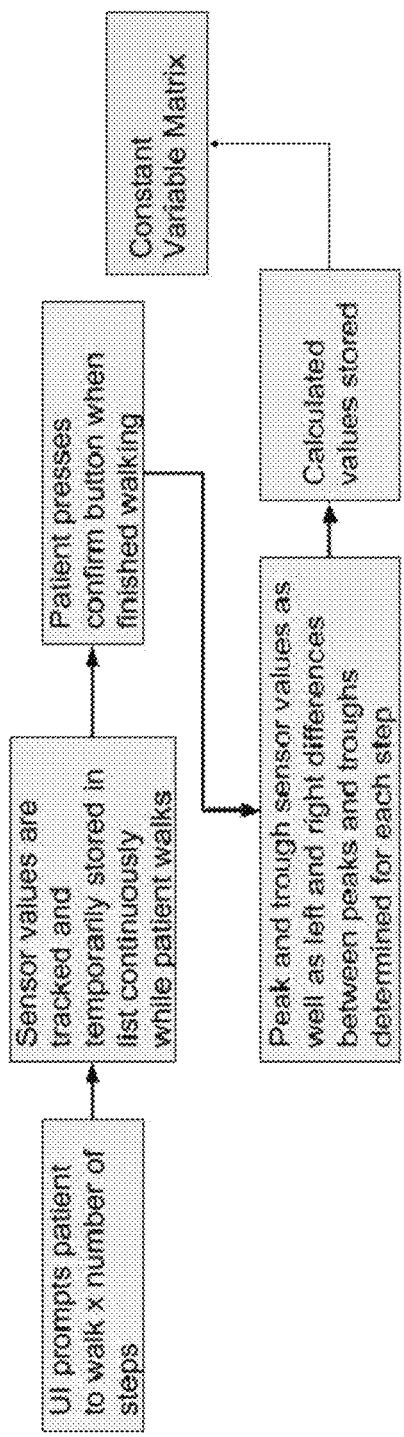
FIG. 5 is an example algorithm flow chart for sleeve calibration.

FIG. 5 shows an example algorithm flow chart for sleeve calibration. Separate wearables 100 may be calibrated to individual patients. A patient's individual sleeve may learn the behavior of that specific patient's joint over time. During an initial consultation with a doctor or therapist, a patient may undergo calibration tests. The medical attendant may instruct the patient to perform a gait assessment, or a series of exercises such as squatting, or leg lifting while sitting, or other join movement sequences that provide information about movement in a specific direction or associated with a specific tendon or rehabilitation goal. The patient will perform the series of motions while wearing the sleeve. Calibration exercises may collect the following parameters: initial gait style, torsion ability, range of motion values, and step length, for example. While the patient performs the assessment, the device receives and stores sensor values. Each assessment may be calibrated for a number of times.

Figure 6A:
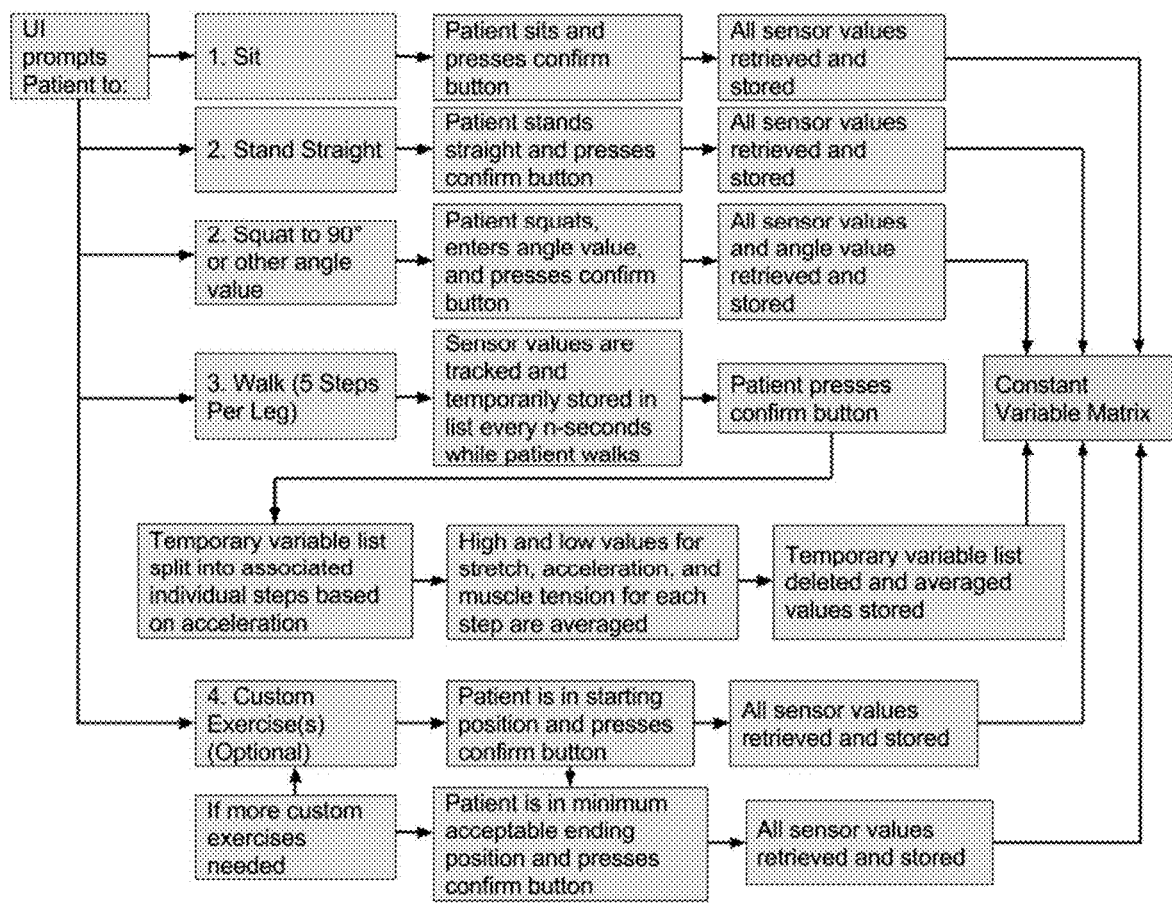
FIG. 6A is another example algorithm flow chart for sleeve calibration.
Figure 6B:
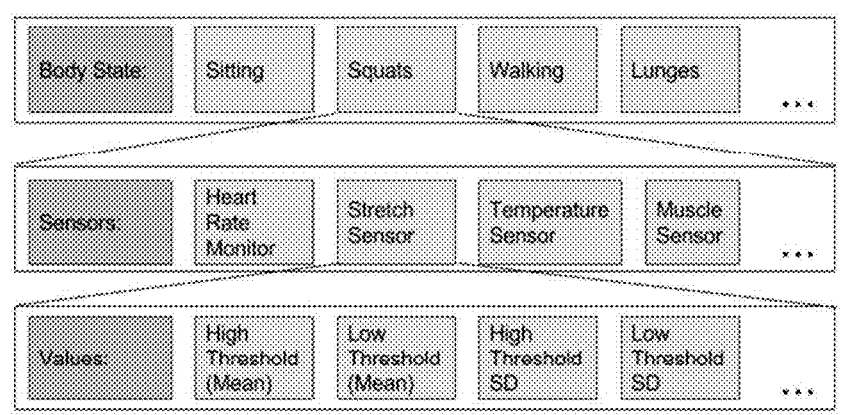
FIG. 6B is a diagram of a device input storage matrix.

FIG. 6A shows another example algorithm flow chart for sleeve calibration. FIG. 6B is a diagram of a device input storage matrix. Once calibration has ended, the wearable's onboard programming may calculate an average of the collected sensor values and determine thresholds based on the set of calibrations with a set standard deviation of two above the range (above or below) of threshold values for the exercise. The application's graphical interface may compare real-time data to the historical record of the joint for easy analysis and understanding of progress.

Calibration exercises may automatically correct for temperature differences and hysteresis following rapid movement. Personalized baselines may be established for longitudinal monitoring relating to success or failure to reach rehabilitation goals, or to provide out-of-bound alerts associated with impending medical complications. These include swelling, abnormal range of joint motion, high acceleration associated with a fall, and temperature imbalances associated with thromboembolism or infection.

Figure 7:
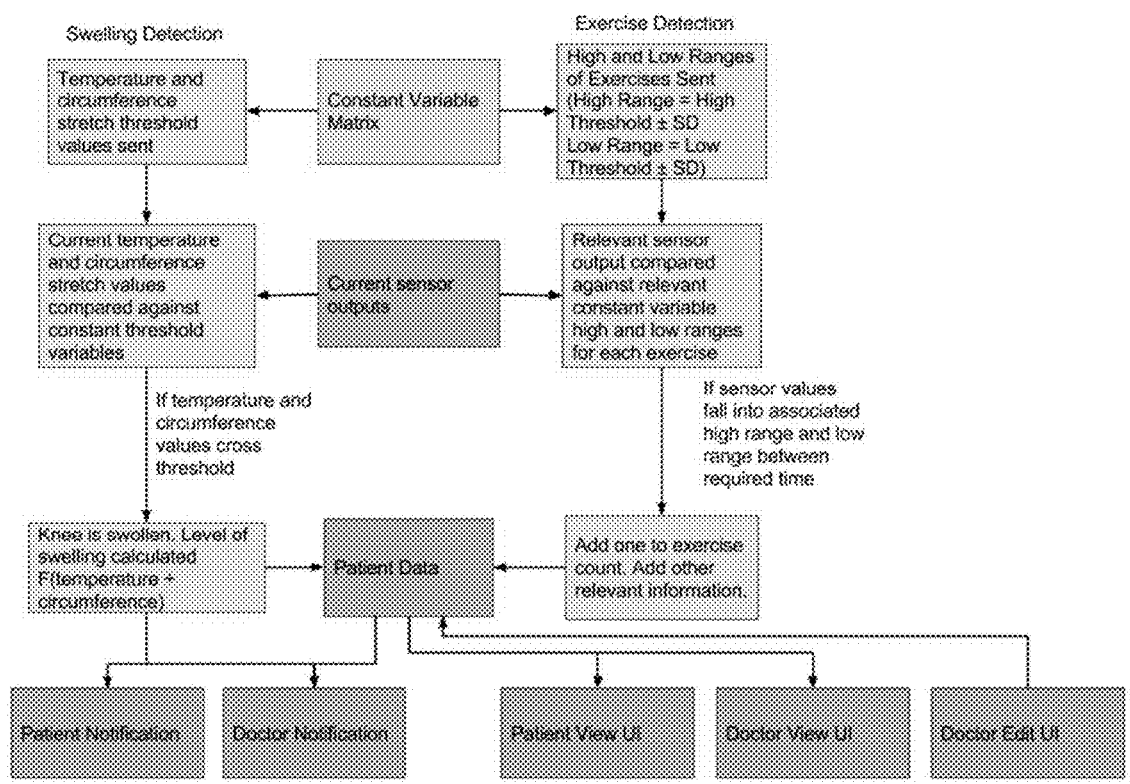
FIG. 7 shows an example algorithm flow chart for swelling detection and exercise detection.

FIG. 7 shows an example algorithm flow chart for swelling detection and exercise detection. The detection methods use current real time sensor outputs together with a constant variable matrix generated during calibration (see FIGS. 5 and 6). The constant variable matrix is used to generate patient specific thresholds. The real time sensor readings are compared to these thresholds to detect abnormalities. For example, the process may detect localized elevations in body temperature by monitoring the temperatures sensed by the temperature sensors at the at least two different positions on the wearable 100. The process may detect swelling by monitoring the strain sensed by the at least one stretch sensor of the wearable 100. The process may identify a risk of thrombosis or infection when one or more of localized elevation in body temperature and swelling are detected.

Real-time changes in the data falling out of expected ranges compared to historical data generate notifications or alerts to the patient and the doctor. These warnings indicate an injury impact, a life-threatening complication, or a severe abnormal direction or range of movement by the joint— factors which can prolong recovery or chance of reinjury and prolonged non-deployable status. During rehabilitation, the device may coach the patient to use the joint and notify the physician about the status of target goals. A common source of pain is anterior knee pain. The patellar monitoring sensor will record patellar deviations that correlate with time periods in which the anterior knee pain is felt. The timing of the pain can in turn be correlated with the readings of the other sensors. The outcome can be a change in the rehabilitation schedule that minimizes or prevents the pain.

The application's graphical interface compares real-time data to the historical record of the joint for easy analysis and understanding of progress. Real-time changes in the data falling out of expected ranges compared to historical data generate alerts to the patient and the doctor. These warnings indicate an injury impact, a life-threatening complication, or a severe abnormal direction or range of movement by the joint—factors which can prolong recovery or chance of re-injury and prolonged non-deployable status.

Figure 8:
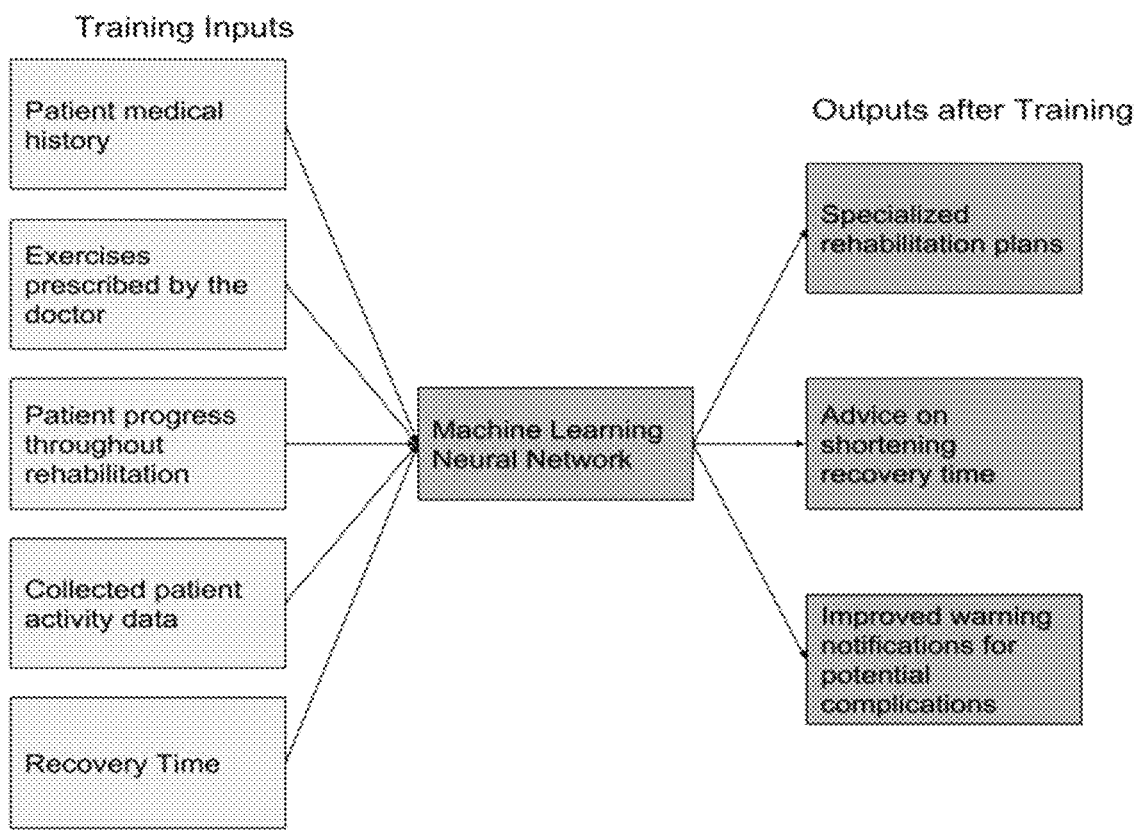
FIG. 8 is a diagram for a machine learning algorithm, in particular a convolutional neural network, which uses collected patient data to improve rehabilitation procedures and outcomes.
Figure 10D:
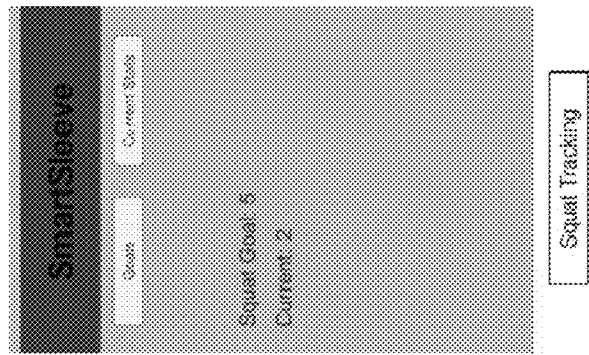
FIGS. 10A to 10D are further example interfaces.
Figure 10C:
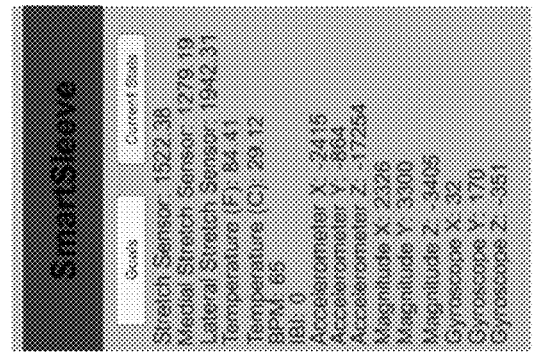
Figure 10B:
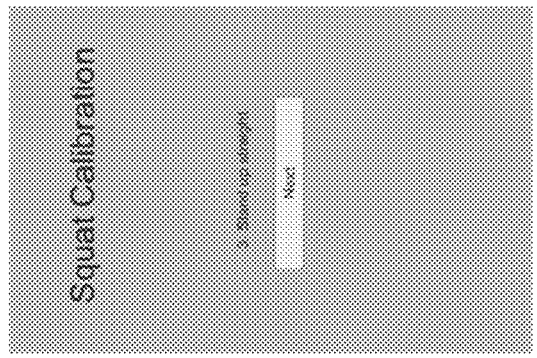
Figure 10A:
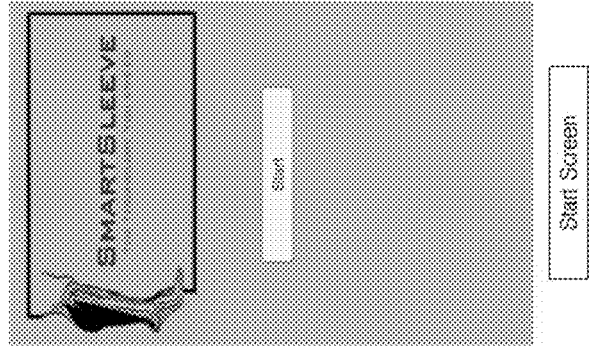

FIG. 8 is a diagram for a machine learning algorithm, in particular a convolutional neural network, which uses collected patient data to improve rehabilitation procedures and outcomes. While a default or individualized standard course of rehabilitation may be recommended for an individual patient clinical study, the data from groups of patients correlated with outcomes may be analyzed with machine learning to develop new classes of rehabilitation regimens for future patients. Such a specialized recovery plan may be the result of correlating physiologic measurements, patient behavior factors, and training inputs, that most influence recovery.

Convolutional neural networks (CNN) can be trained on data involving the frequency of various exercises performed by patients and the duration of recovery to identify which exercise plans result in a quicker recovery. In this manner wearables 100 may help future patients with histories similar to past patients, by, for example, suggesting rehabilitation plans that are expected to be the most beneficial to the patient's recovery, and offering specific corrections to a patient's activity or inactivity that may hinder their recovery process.

Progress toward rehabilitation may be computed based on sensor data from a subject's wearable and reference data. Data retrieved from sensors (e.g., of a wearable 100) may be compared with reference data in a databank which specifies parameter thresholds corresponding with rehabilitation progress levels. A computation of progress toward rehabilitation based on data retrieved from sensors may determine whether data for one or more physical or physiological parameters approach a stored normal or baseline measurement for similar subjects or a baseline measurement for the particular subject obtained prior to injury or surgery. Improvement to within 10, 9, 8, 7, 6, 5, 4, 3, 2, or 1% of the normal or baseline measurement can be an indication of rehabilitation of the joint.

Embodiments may involve integration and linkage with patient's medical data. Data sets from multiple users may be analyzed to improve rehabilitation care procedures and monitoring. These data sets may include information such as a patient's basic medical history, progress meeting goals of exercises prescribed by the doctors, and the rate of patient progress throughout rehabilitation. The full record of monitored sensor data, and time to recovery will be part of the patient record.

FIGS. 9A-9C and FIGS. 10A-10D show non-limiting example interfaces. An exemplary system provides for a rapid, easy to understand interface for the patient as well as an individual view and multi-patient dashboard for a supporting medical team. Real time and historical data may be presented in a friendly easy to understand interface on the patient's smartphone. Outputs on a user interface may include reminders and encouragements based on customized rehabilitation regimens loaded by a medical team.

Patient prompts and encouragements may be output through a patient interface to achieve preset milestones. The software may interact with patients to encourage coaching, milestones, and rehab assignments designed by a specialist. For example, on a phone app, the patient may be coached through walking and knee motion exercises, while simultaneously monitoring relevant physiologic parameters such as number and rate of steps, range and direction of motion, tissue temperature imbalances, swelling, and acceleration force. Physicians and physical therapists may add patient data, such as height and weight, and a personalized rehabilitation plan, with specific goals and exercises, to the phone application. Integrated software will calibrate the sensors to the baseline measurements during initial fitting of the device.

Advanced predictive algorithms may instruct, manage, and track patient rehabilitation. Precise, encrypted, quantitative data is collected by the sleeve and transmitted via Bluetooth, radio telemetry, or WiFi using secure military software to both the physician and patient's applications for rehabilitation guidance and alarms, for example. For medical specialists, a unique cohort dashboard may display the rehabilitation progress of a set of individuals currently receiving rehabilitation.

EXAMPLES

The following are non-limiting examples which discusses one or more prototype embodiments demonstrating functionality.

Example 1

Figure 11:
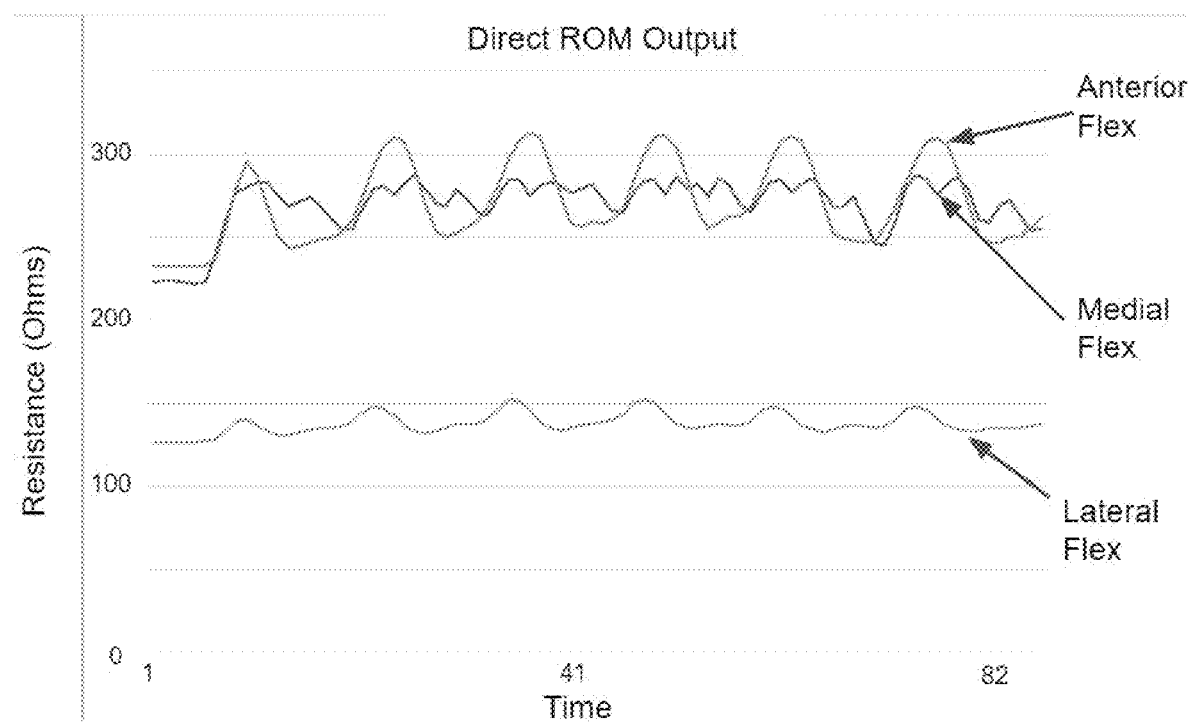
FIG. 11 was flexion/extension walking pattern derived from example volunteer wearing the device. The resistances of each flex/stretch sensor and their positions or anatomical locations are noted. Note, the highly reproducible peak/valley signal dynamics between each step.
Figure 12:
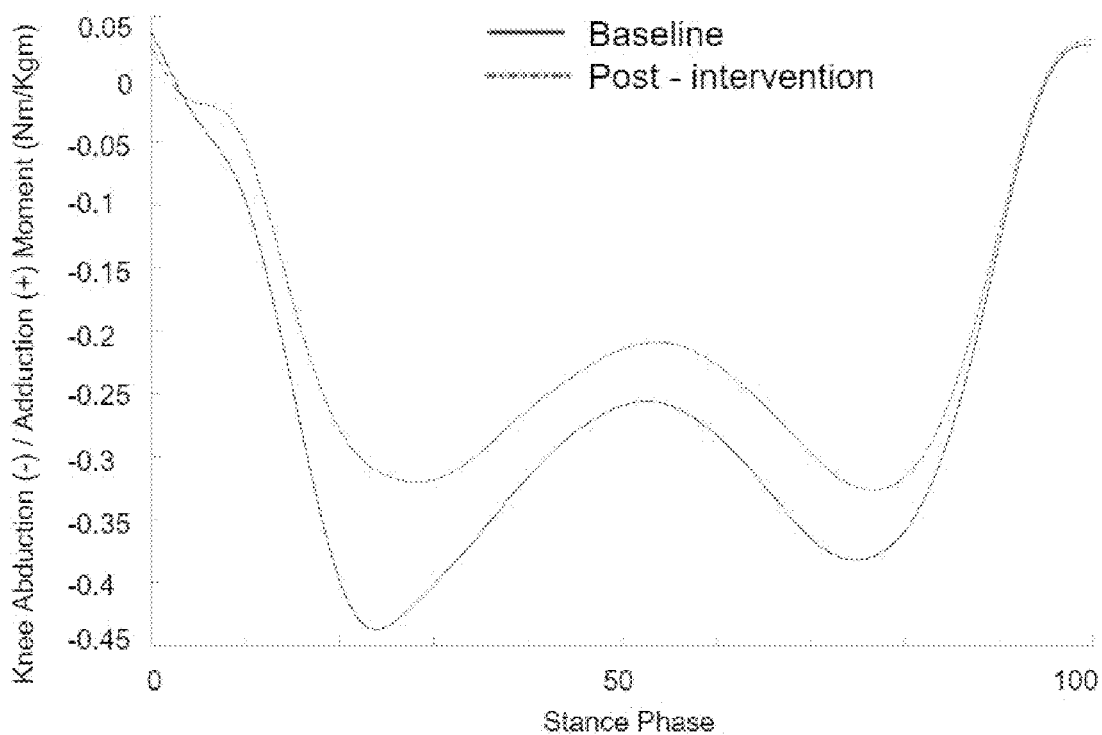
FIG. 12 is independent confirmation of knee joint motion dynamics for a single step using an external 3D motion capture camera from George Mason University's (GMU's) rehabilitation center "SMARTLab".

Biomechanical Analysis: A prototype device was tested with normal volunteers. FIG. 11 shows lab walking data taken from reproducible steps. The pattern of flexion/extension is characteristic of the anatomical locations of the flex sensors. The kinematic data was independently verified with a 3D gait assessment. The oscillatory example volunteer wearing the device displays the stretch and flex data 5 changes (peak sand valleys) of the device correlate with a single step taken with 3D motion capture, (FIG. 12) that correspond to an individual knee flexion for one step.

Figure 13:
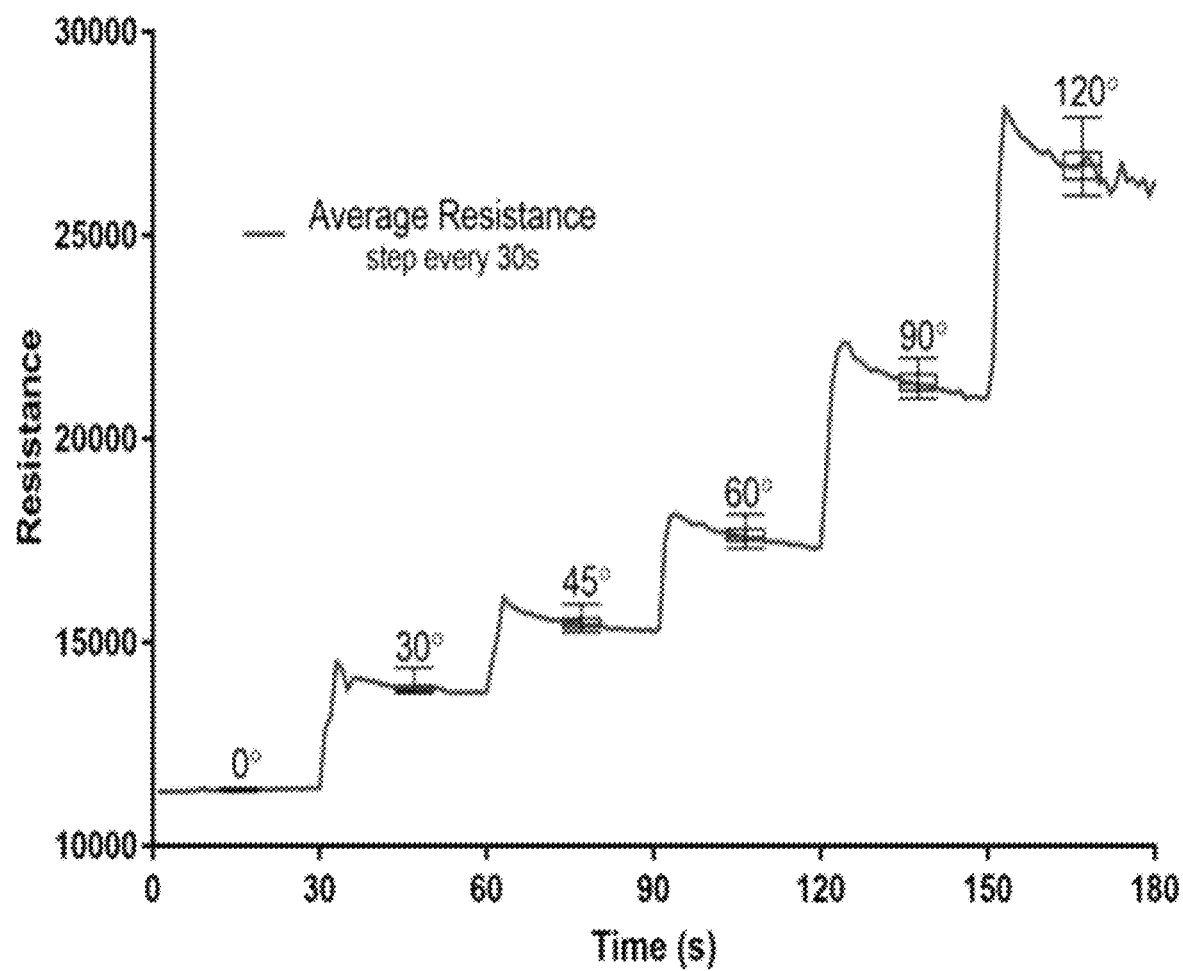
FIG. 13 is precision studies between range of motion (ROM) for a subject wearing the sleeve. The resistance of the flex sensor was calibrated to flexion/extension angles of the knee. Comparison is shown for the resistance of the flex sensor to the movement between the listed angles measured independently using a goniometer. Note the high precision along the full ROM.

Range of Motion: Precision coefficient of variation (CV) for ROM in degrees was validated and is shown for an example individual between-run study (FIG. 13). The sensor output was compared to a standardized goniometer to measure joint angle independently while the sleeve device simultaneously was calculating the joint angle via flex resistances.

The device was compared to the calculated angle and was shown to be highly concordant with very low CVs.

Figure 14:
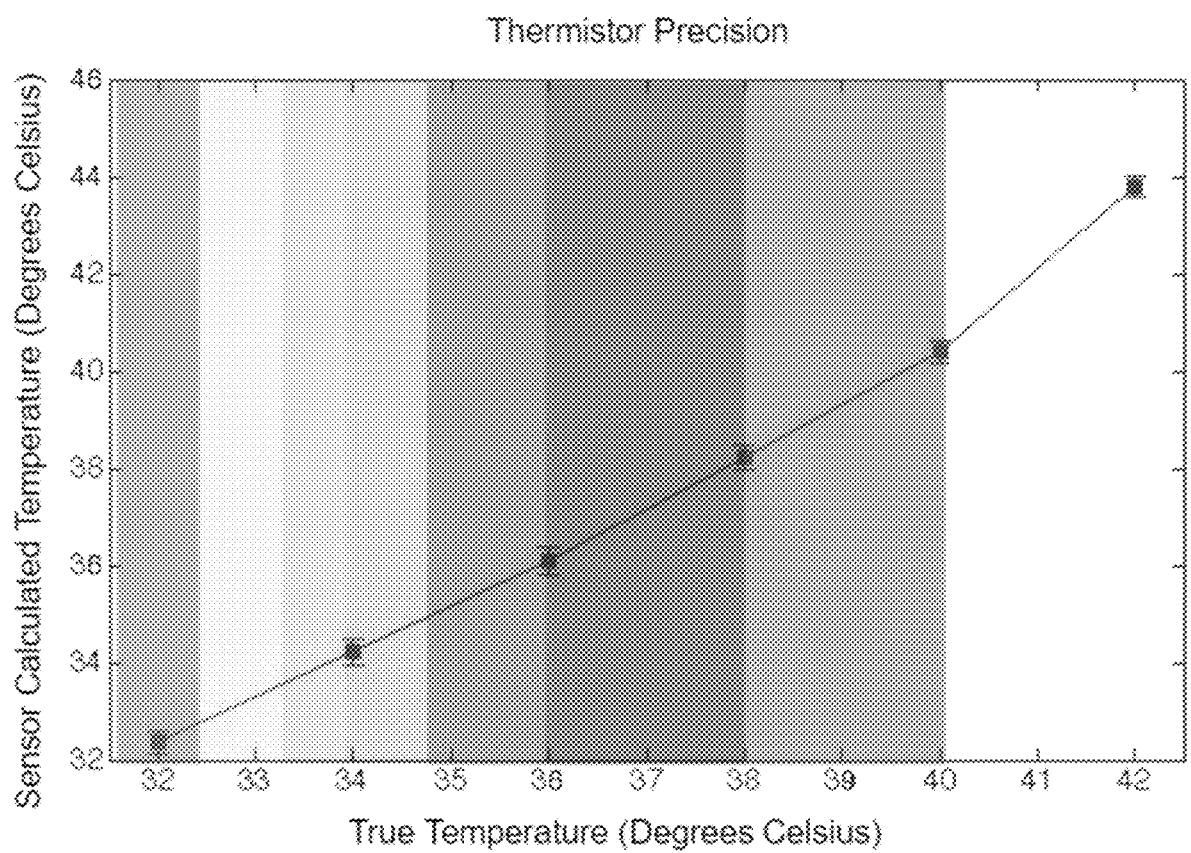
FIG. 14 shows temperature accuracy and precision measured by the NTC thermistor over the dynamic range of 32-42 degrees Celsius.
Figure 15:
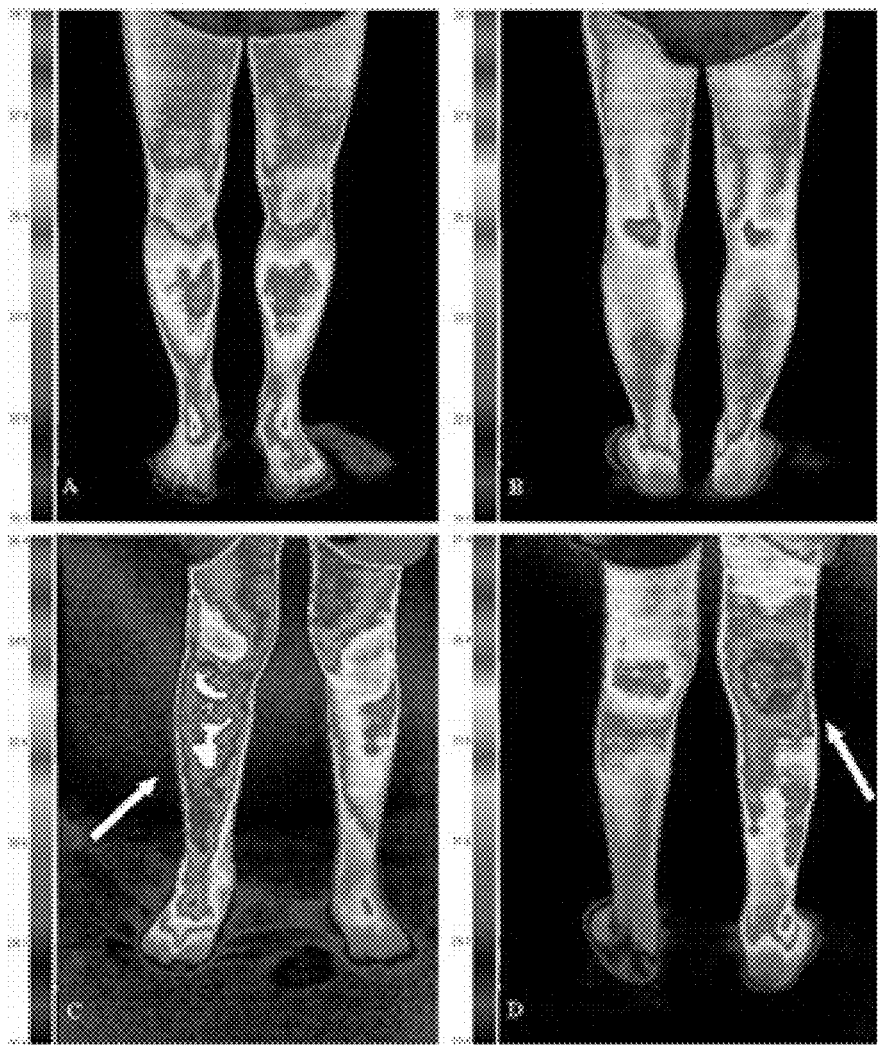
FIG. 15 shows infrared thermography comparing a leg with thromboembolism to the normal contralateral knee. Note, the temperature resolution of the thermistor exceeds the resolution required to detect abnormal temperature differences.

Temperature: A NTC thermistor encapsulated by silicon was used for this test device. This particular thermistor, compared to a series of commercial temperature sensors we evaluated was found to have high precision and a high resolution. Calibrated against temperatures in the appropriate physiologic range, the NTC thermistor resolution, accuracy and precision, greatly exceeds physiological temperature variations relevant for rehabilitation, see FIG. 14. A <0.99 R correlation between actual temperature and calculated temperature with a CV of <0.02 precision. The critical detection temperature range and small deviations concordant with DVT, infection, or injury can readily distinguish by this sensor, see FIG. 15. The thermistors positioned in an array surrounding the joint, as shown in FIG. 1B, permit a collection relative temperature differences between important anatomic regions of the knee normalized against the patellar surface as a baseline.

Figure 16:
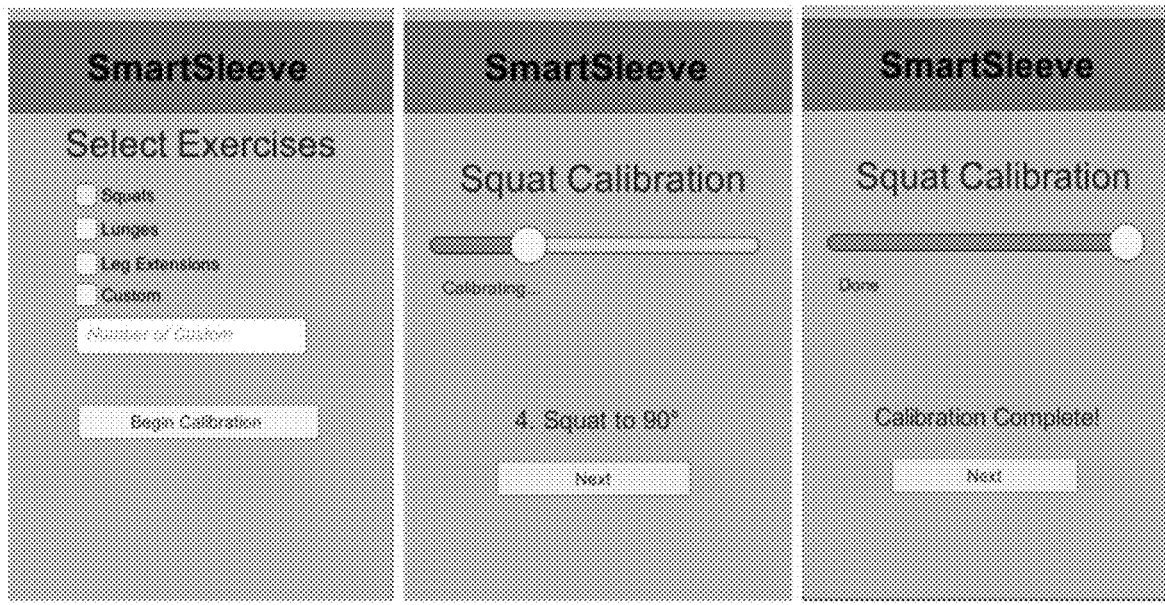
FIG. 16 is (top) calibration graphical interface of the prompts for completing device calibration and (below) the data displayed indicates that the software can independently detect the correct type of exercise task performed during the calibration procedure.

Calibration Software Feasibility: To verify the accuracy of the calibration software with correctly identifying the exercise movements collected, a volunteer wore the device during the calibration mode. The user was instructed to perform 20 squats. The calibration algorithm had a total of error of 4% for 5 trials as shown in FIG. 16.

Example 2

Kinematic and biomechanical measurements for the IMU/accelerometer and flex/stretch sensors may be verified using 3D gait analysis. Ten calibration markers are placed on anatomical landmarks including the left and right greater trochanter and the midline of knees and malleoli. Once markers are placed, a static trial is taken to establish a baseline orientation. All kinematic data is collected at a sample rate of 200 Hz using a Vicon motion analysis system (Oxford Metrics Ltd., Oxford, UK). From the static trial, a kinematic model is created for each participant using Visual 3D software (C-Motion, Germantown MD, USA) which includes the trunk, pelvis, thigh, shank, and foot segments.

The kinematic model created in Visual 3D is used to quantify the motion at the hip, knee, and ankle joints with rotations being expressed relative to the static trial. A cardan angle sequence was used to calculate joint angles and a standard inverse dynamics analysis was conducted to synthesize the trajectory. Joint kinematics and kinetics will be filtered at 8 Hz to reduce the effects of artifacts based on our laboratory results from residual analysis. Joint angles will be measured in degrees, and all internal joint moments will be normalized to mass and height (Nm/Kgm). We will also quantify spatio-temporal variables using the motion capture system, such as step length, step width, and gait speed. All gait trials will be normalized to 100 percent of stance. Mean values will be computed and used for all statistical analyses. During the first phase, all gait assessments are conducted over force platforms (or instrumented treadmill) to determine gait events that can distinguish gait phases (e.g., stance, swing). Subsequent to this initial validation, a subsample of participants use the wearable as well as Inertial Measurement Units (e.g., IMeasureU—IMUs) outside the laboratory to validate impact forces in ecologically valid environments.

Expected measurement ranges and power calculation for kinematic studies. Power calculations for athletic tasks of the type proposed was conducted to estimate the sample size needed to establish significant differences between measurements derived from two different athletic tasks being compared. Using data for or a power level of 80% and an alpha of 0.05, the necessary sample size is 19 participants. As indicated in the following table, nineteen female collegiate soccer players (age. 19.6+ 0.8 years; height. 1.67+ 0.05 m; mass. 63.7+ 10.1 kg) from a Division I institution were chosen to participate in this study.

TABLE 1

Descriptive analysis (means of five trials, and SD) of the kinematic variables at initial contact, peak posterior ground reaction force (PGRF), and peak stance during two athletic tasks using two landing-techniques. All variables measured in degrees.

| | Sidestep | | | | | Pivot | | | | |
| --- | --- | --- | --- | --- | --- | --- | --- | --- | --- | --- |
| | Forefoot | | Rearfoot | | | Forefoot | | Rearfoot | | |
| | Mean | SD | Mean | SD | P | Mean | SD | Mean | SD | P |
| Initial contact | | | | | | | | | | |
| Knee flexion (−)/extension (+) | −42.0 | 10.3 | −33.1 | 6 | <0.001* | −25.9 | 7.8 | −17.8 | 5 | <0.001* |
| Knee valgus (−)/varus (+) | −0.7 | 11.2 | −3.1 | 9 | 0.031* | −12.8 | 7.9 | −7.4 | 6.7 | <0.001* |
| Hip flexion | 49.5 | 10.6 | 55.1 | 8.3 | 0.033* | 46.5 | 8 | 50.7 | 6.9 | <0.001* |

TABLE 1-continued

Descriptive analysis (means of five trials, and SD) of the kinematic variables at initial contact, peak posterior ground reaction force (PGRF), and peak stance during two athletic tasks using two landing-techniques. All variables measured in degrees.

| | Sidestep | | | | | Pivot | | | | |
|---|---|---|---|---|---|---|---|---|---|---|
| | Forefoot | | Rearfoot | | | Forefoot | | Rearfoot | | |
| | Mean | SD | Mean | SD | P | Mean | SD | Mean | SD | P |
| PPGRF | | | | | | | | | | |
| Knee flexion (−)/extension (+) | −50.2 | 7.8 | −48.4 | 7 | >0.05 | −41.1 | 12.3 | −30.3 | 8.7 | <0.001* |
| Peak stance | | | | | | | | | | |
| Knee flexion (−)/extension (+) | −53.7 | 7.1 | −56.1 | 5.4 | 0.012* | −58.6 | 9.3 | −54.6 | 8.4 | >0.05 |
| Knee valgus (−)/varus (+) | −3.6 | 11 | −4.8 | 8.6 | >0.05 | −14.4 | 8.2 | −8.4 | 7.3 | <0.001* |
| Hip flexion | 50 | 9.8 | 57.3 | 7.8 | 0.006* | 58.2 | 12.4 | 66.3 | 10.4 | <0.001* |

*Statistical difference between landing techniques within each athletic task.

Figure 17:
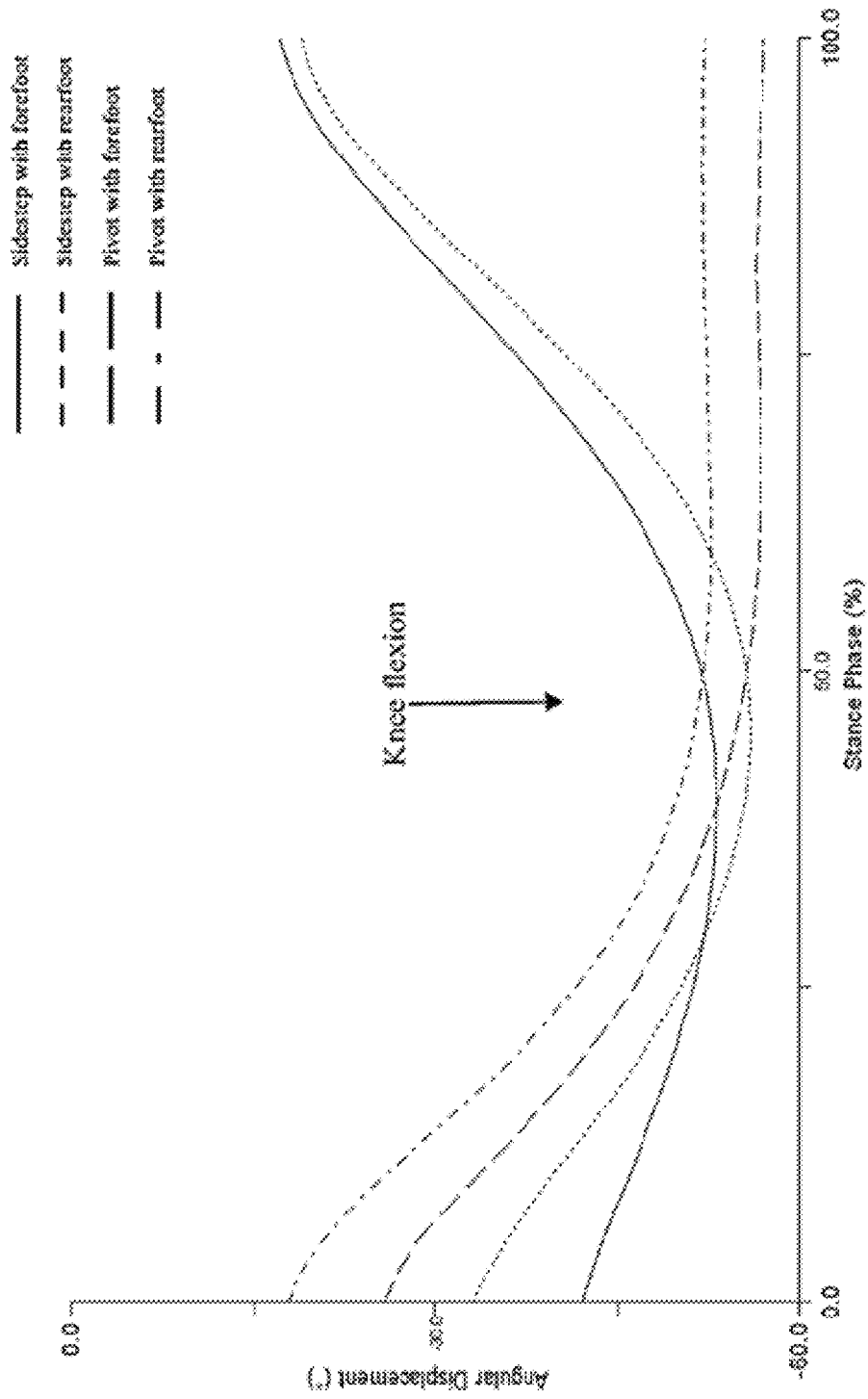
FIG. 17 is changes observed in knee flexion angular displacement in degrees across the two tasks: side step, pivot and landing techniques (rearfoot, forefoot). Angular displacement curves during the stance phase. Each curve represents the mean normative value of the entire sample.

Participants were screened to ensure none had any previous hip, low back, knee, or severe ankle injuries within the previous 6 months or surgeries within the last 2 years. Participants completed a 5-min cycling warm-up and 5 min of self-directed stretching. General anthropometric measures were taken for each participant. Reflective markers were placed on specific body landmarks according to a modified Helen Hayes marker set. A standing (static) trial with the participants standing on the force plates with shoulders abducted at 908 was obtained. The static trial was later used to compute the kinematic model. Participants were required to conduct three movement tasks: drop-jump, sidestep cutting, and pivoting maneuver. The pivot task had lower knee flexion (741.2+8.88) and a higher valgus angle (77.6+10.18) than the sidestep (753.9+9.48 and 72.9+10.08, respectively) at maximum vertical ground reaction force. The pivot task (0.8+0.3 multiples of body weight) had higher peak posterior ground reaction force than the drop jump (0.3+0.06 multiples of body weight) and sidestep cutting (0.3+0.1 multiples of body weight), as well as higher internal varus moments (0.72+0.3 N m/kg m) than the drop-jump (0.14+0.07 N m/kg m) and sidestep (0.17+0.5 N m/kg m) at peak stance. The pivot task presented a lower knee extension-flexion moment (p<0.001) and higher knee varus-valgus moment (p<0.001) than the drop-jump and sidestep tasks at initial contact. Knee extension moment peak stance was higher for the sidestep (p<0.001) than for the drop-jump and pivot, and was higher for the drop-jump than the pivot (FIG. 17). These data and the established sports tasks were a comparison basis for testing a wearable according to the invention in a laboratory under the same conditions.

Expected measurement ranges and power calculation for thermal mapping studies:

Infrared thermal imaging (IRTI) has been used to detect DVT and diseases. IRTI testing was conducted in a temperature controlled room. As shown in the feasibility data (FIG. 14), the between run precision (CV<0.02) and accuracy (R>0.99) of the temperature measurements conducted using the sleeve thermistor exceeds the requirements necessary for detecting the measured temperature differences associated with thromboembolism of 0.5 degrees C. over a range of 32.0 to 42.0 degrees C. Consequently, the power calculation for thermal imaging for any individual anatomic temperature difference between the injured knee and the opposite non-injured knee in the same patient for a power level of 85% and an alpha of 0.05, the necessary sample size is 20 participants.

Expected measurement ranges and power calculation for patella displacement: In addition to the superior and inferior motion of the patella, the patella also tracks lateral-medial during tibiofemoral extension to flexion. Therefore the type of measurements for the patella proposed for the wearable device, in all four directions, is an innovative approach to identify situations in which excessive medial or lateral motion occurs during flexion, since the patella remains relatively centered on the trochlea in normal or athletic use. Excessive dynamic knee valgus is an abnormality of neuromuscular control over the lower limb. This creates a lateral force vector on the patella and increases the compressive loads between the lateral face of the patella and the lateral femoral condyle. Studies have demonstrated that patients with patella femoral pain syndrome present greater dynamic knee valgus than do controls without. Power calculations for expected patellar displacement values will be based on Ota et al 2018. A modified patellofemoral arthrometer is usable, and the procedure of Ota et al 2018 is used to validate the patellar force sensor. In the Ota study passive lateral and medial patellar displacement was measured on 103 men and 102 women using a modified patellofemoral arthrometer and manual pushing method at 0° and 30° knee flexion angles. The absolute values of lateral and medial patellar displacement (LPD and MPD, respectively), and values normalized to patellar width (PW) and body height (HT) revealed that at 30° knee flexion angle, LPD/PW and LPD/HT were greater in women than in men (LPD/PW: 27.0±6.7% vs. 22.6±6.7%, LPD/HT: 0.81±0.19% vs. 0.70±0.15%, respectively, P<0.001, effect size >0.50). Absolute and normalized lateral and medial patellar mobility correlated positively with the range of the knee extension angle. A patella displacement range discrimination is expected to span displacements with a precision of ten percent to achieve a power level of 80% with an alpha of 0.05 and an N=100.

Data Analysis: All trials are normalized to 100% of stance phase. All data are reduced using MATLAB (The Math Works, Inc., Natick, MA, USA) with the creation of a custom made program to export the dependent measures into a Microsoft Excel spreadsheet. Groups of trials, or individual between run and within run is averaged and exported into PASW version 18.0 (IBM Corporation, Somers, NY, USA) for data analysis. A Bonferroni adjustment for multiple comparisons is used with an adjusted alpha level set a priori at 0.025. Separate repeated measures analyses of variance (ANOVA) with landing technique (2 levels; rearfoot and forefoot) as example repeating factors, are conducted to evaluate the kinematic and kinetic parameters. These parameters are evaluated at different time instants for each task. Specifically, initial contact includes: knee flexion, valgus, hip flexion, knee flexion and abduction moment, and posterior ground reaction force. Peak posterior ground reaction force included: knee flexion and posterior ground reaction force. Peak stance includes: knee flexion, valgus angles, hip flexion, and knee flexion and abduction moment. Peak vertical ground reaction force is also measured. The stance phase is defined from initial contact, as the moment where vertical ground reaction force is higher than 10 N, until toe-off from the force plate. Peak stance is defined as the maximum value of a dependent measure between initial contact and 50% of stance phase ground reaction forces were normalized to bodyweight while joint moments are normalized to mass and height (Nm/kgm). Independent variables included tasks (sidestep and stop-jump) and measurement type (external (e.g. 3D motion camera, IR camera, patella deviation measurements or internal (derived from the sleeve sensor). The dependent variables in the task include: vertical and posterior ground reaction forces, knee flexion, knee abduction, knee rotation, knee flexion-extension moment, knee abduction-adduction moment, hip flexion, hip abduction, and hip flexion moment. Analysis of variance (ANOVA) is conducted for each dependent variable. Data will also be analyzed by Friedman's non-parametric test and followed by post-hoc analysis by the Wilcoxon Signed-Rank test. Power calculations, as justified above by sensor measurement accuracy, linearity and precision for each measurement type, will assure a power level greater than or equal to 80% with an alpha of 0.05. Between run, within run, linearity, precision, and outcome correlation studies will follow strict CAP/CLIA guidelines.

Example 3

The patellar sensor shown in FIGS. 3A and 3B is used in conjunction with the other measurement systems or as a stand-alone piece for producing data for the following applications:
1) The individualization of the placement of the sleeve surrounding the joint: A major need in knee sleeve sensing is to ensure that the sensors are distributed in the same position each time the wearer puts the device on. One of the roles of the patellar sensor is to sense that the device of which the patellar sensor is a part is correctly placed so that the patella is surrounded by the pressure donut and able to provide feedback to the user to rotate or adjust the sleeve to correctly fit around the patella. This molding to an individual's knee allows a standardization of the knee sleeve position each time it is worn.
2) Real time measurements of patellar tracking during rehabilitation exercises or during general movements of the knee: Within the patellar sensor are integrated force and temperature sensors which provide data concerning the position of the patella on all axis of direction and measurements of the temperature profile of the tissue surrounding the patella. The information recorded from the patellar sensor is transmitted to the CPU and mobile application for comparison to the patients input of pain levels and rehabilitation specialists' notations, such that the position of the patella with or without the contribution of the other sensors can guide the menu of rehabilitation exercises prescribed for the patient such that painful movements can be avoided or causes of biomechanical or physiological pain can be determined. Force and direction measurements of the patella can be measured according to the criteria within Example 2.
3) Patellar temperature measurements as a ground state baseline for temperature differentials associated with thromboembolism. Temperature in the posterior region of the knee and temperatures measured anteriorly in Examples 1 can be used to determine thromboembolism. Specifically, the invention's patellar sensor has temperature sensors within the pressure donut which are used in conjunction with the other sensors mapped around the sleeve for recognition of a thromboembolism event. The baseline temperature sensing may be in the range of 31-33 degree Celsius in the patella region. If the temperature in the posterior region of the knee and in the inferior, anterior (shin) in the becomes elevate above the patella baseline, for example achieving a value of 36 to 40 degrees Celsius, this indicates a high likelihood of a thromboembolism occurring. An additional measurement can be contributed by the stretch sensor placed inferior to the knee joint. If this stretch sensor is lengthened this will indicate a swelling. Such effusion or vein thrombosis expansion and associated tissue heat and swelling is indicative of a thromboembolism event, particularly when associated with a significant temperature differential near the patella compared to the region of underlying thrombosis. The temperature differentials and stretch measurements are done to achieve a high sensitivity and specificity for thromboembolism detection.

The combination of measurements are useful in rehabilitation in the following example: A patient is fitted with the knee sleeve and feedback is given through the mobile application privately or in the presence of rehabilitation personnel to ensure that the knee sleeve is positioned correctly over the patella. These values are stored and remembered to inform a patient if they are correctly wearing the device. The patient is then presented with a menu of specific calibration exercises to perform for device calibration. The pressure and force changes in the patella in conjunction with stretch sensors and circumferential temperature sensors are used to calibrate the sensor. The patient then follows a series of rehabilitation exercises with milestones for range or motility, levels of acceptable pain, and frequency of movement scored by the rehabilitation manager using the wireless information data provided by the sleeve. In another example case, it is noted from the sensor data that patella tracking laterally is associated with a high degree of anterior knee pain during rehabilitation exercises. The rehabilitation manager uses this information to change the exercise regimen to reduce the movement of the patella in this plane to reduce the pain thereby improving the rehabilitation compliance. In addition, after the rehabilitation exercise session, when the patient is at home, the temperature sensors in the patellar sensor region are compared to the temperature sensors in posterior region and stretch sensors in the inferior region of the device to monitor differential temperatures or stretch indicative of thromboembolism. When the device detects this event it issues an alert to the doctor wirelessly, noting this life threatening complication has occurred. The patient is then directed by phone or application to go to emergency room for immediate treatment.

While the invention has been described in terms of exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

What is claimed is:

1. A device, comprising
a wrap for a joint of a patient's body, wherein the joint is a knee, elbow, wrist, hip, ankle, or shoulder;
temperature sensors attached or attachable to the wrap, the temperature sensors comprising a first temperature sensor configured to sense a first temperature in a first position on the wrap and a second temperature sensor configured to sense a second temperature in a second position on the wrap, wherein the first position corresponds with a back of the joint and the second position corresponds with a front of the joint; and
at least one processor and storage, the storage comprising executable instructions which, when executed by the processor, cause the at least one processor to detect an elevation between the first and second temperatures indicative of an embolism and determine a diagnostic output of an embolism based on the elevation.

2. The device of claim 1, wherein the storage comprises further executable instructions which, when executed by the at least one processor, cause the at least one processor to determine a therapeutic output based on the elevation.

3. The device of claim 1, wherein the storage comprises further executable instructions which, when executed by the at least one processor, cause the at least one processor to provide an alert of a health risk implicated by the elevation.

4. The device of claim 3, wherein the health risk is an embolism.

5. The device of claim 1, wherein the joint is a knee.

6. The device of claim 5, wherein the second position corresponds with a patella of the knee.

7. The device of claim 1, further comprising one or more stretch sensors.

8. The device of claim 7, wherein the storage comprises further executable instructions which, when executed by the at least one processor, cause the at least one processor to detect a change indicative of swelling at the joint from signals of the one or more stretch sensors.

9. The device of claim 8, wherein the storage comprises further executable instructions which, when executed by the at least one processor, cause the at least one processor to determine a diagnostic or therapeutic output based on a combination of the elevation and the change indicative of swelling at the joint.

10. A method, comprising
measuring a first temperature at a back of a joint with a first temperature sensor, wherein the joint is a knee, elbow, wrist, hip, ankle, or shoulder;
measuring a second temperature at a second position with a second temperature sensor, wherein the second position corresponds with a front of the joint;
comparing the first and second temperatures from the first and second temperature sensors; and
determining a diagnostic output of an embolism from the temperature comparison.

11. A device, comprising
a first temperature sensor configured to measure a first temperature at a back of a joint, wherein the joint is a knee, elbow, wrist, hip, ankle, or shoulder;
a second temperature sensor configured to measure a second temperature at a second position different than the back of the joint; and
at least one processor and storage, the storage comprising executable instructions which, when executed by the at least one processor, cause the at least one processor to detect an elevation between the first and second temperatures indicative of an embolism and determine a diagnostic output of an embolism from the elevation.

12. The device of claim 11, wherein the storage comprises further executable instructions which, when executed by the at least one processor, cause the at least one processor to determine a therapeutic output based on the elevation.

13. The device of claim 11, wherein the storage comprises further executable instructions which, when executed by the at least one processor, cause the at least one processor to provide an alert of a health risk implicated by the elevation, wherein the health risk is an embolism.

14. The device of claim 11, wherein the joint is a knee.

15. The device of claim 14, wherein the second position corresponds with a patella of the knee.

16. The device of claim 11, further comprising one or more stretch sensors.

17. The device of claim 16, wherein the storage comprises further executable instructions which, when executed by the at least one processor, cause the at least one processor to detect a change indicative of swelling at the joint from signals of the one or more stretch sensors.

18. The device of claim 17, wherein the storage comprises further executable instructions which, when executed by the at least one processor, cause the at least one processor to determine a diagnostic or therapeutic output based on a combination of the elevation and the change indicative of swelling at the joint.

* * * * *